(12) United States Patent
Holley, Jr. et al.

(10) Patent No.: US 9,718,246 B2
(45) Date of Patent: Aug. 1, 2017

(54) CARTON WITH ARTICLE PROTECTION FEATURES

(71) Applicant: Graphic Packaging International, Inc., Atlanta, GA (US)

(72) Inventors: John Murdick Holley, Jr., Lawrenceville, GA (US); Colin P. Ford, Woodstock, GA (US)

(73) Assignee: Graphic Packaging International, Inc., Atlanta, GA (US)

(*) Notice: Subject to any disclaimer, the term of this patent is extended or adjusted under 35 U.S.C. 154(b) by 141 days.

(21) Appl. No.: 14/565,788

(22) Filed: Dec. 10, 2014

(65) Prior Publication Data
US 2015/0158648 A1 Jun. 11, 2015

Related U.S. Application Data

(60) Provisional application No. 61/963,653, filed on Dec. 10, 2013, provisional application No. 61/966,736, filed on Feb. 28, 2014.

(51) Int. Cl.
*B65D 65/00* (2006.01)
*B65D 75/00* (2006.01)
(Continued)

(52) U.S. Cl.
CPC ............... *B31B 1/25* (2013.01); *B31B 1/90* (2013.01); *B31B 7/26* (2013.01); *B31B 11/00* (2013.01);
(Continued)

(58) Field of Classification Search
CPC .... B31B 1/25; B31B 1/90; B31B 7/26; B31B 11/00; B65D 5/32; B65D 5/445;
(Continued)

(56) References Cited

U.S. PATENT DOCUMENTS 1,925,102 A 9/1933 Levkoff
2,005,924 A 6/1935 Wilson
(Continued)

FOREIGN PATENT DOCUMENTS

CA 873185 6/1971
CA 2 610 666 5/2008
(Continued)

OTHER PUBLICATIONS

International Search Report and Written Opinion for PCT/US2015/017959 dated Jun. 16, 2015.
(Continued)

*Primary Examiner* — Jacob K Ackun
*Assistant Examiner* — Rafael Ortiz
(74) *Attorney, Agent, or Firm* — Womble Carlyle Sandridge & Rice, LLP

(57) ABSTRACT

A carton for holding a plurality of containers. The carton can comprise a plurality of panels that extends at least partially around an interior of the carton. The plurality of panels comprises a top panel. An insert can comprise a central panel, an inner end flap foldably connected to the central panel, and at least one crown guard flap foldably connected to the inner end flap adjacent a crown guard opening in the insert. The central panel can comprise a stop edge adjacent the crown guard opening, and the crown guard flap can comprise a first portion foldably connected to the inner end flap and a second portion foldably connected to the first portion. The top panel can at least partially overlap the central panel, and the second portion of the crown guard flap can be disposed adjacent the stop edge of the central panel.

23 Claims, 21 Drawing Sheets

(51) Int. Cl.
    *B31B 1/25*     (2006.01)
    *B65D 5/32*     (2006.01)
    *B65D 5/44*     (2006.01)
    *B65D 5/468*     (2006.01)
    *B65D 5/50*     (2006.01)
    *B65D 5/54*     (2006.01)
    *B31B 11/00*     (2006.01)
    *B31B 7/26*     (2006.01)
    *B31B 1/90*     (2006.01)

(52) U.S. Cl.
    CPC ............. *B65D 5/32* (2013.01); *B65D 5/445* (2013.01); *B65D 5/4608* (2013.01); *B65D 5/5028* (2013.01); *B65D 5/541* (2013.01); *B65D 5/5415* (2013.01)

(58) Field of Classification Search
    CPC .... B65D 5/4608; B65D 5/5028; B65D 5/541; B65D 5/5415
    USPC ..... 206/433, 427, 434, 435, 784; 229/103.2, 229/117.09, 199, 120.33–120.38
    See application file for complete search history.

(56) References Cited

U.S. PATENT DOCUMENTS

| | | |
|---|---|---|
| 2,067,749 A | 1/1937 | Zimmerman et al. |
| 2,115,673 A | 4/1938 | Stompe |
| 2,196,502 A | 4/1940 | Kells |
| 2,299,027 A | 10/1942 | Novak |
| 2,386,905 A | 10/1945 | Meitzen |
| 2,648,484 A | 8/1953 | Belsinger |
| 2,669,351 A | 2/1954 | Carson et al. |
| 2,754,047 A | 7/1956 | Schmidt et al. |
| 3,078,032 A | 2/1963 | Robinson et al. |
| 3,128,010 A | 4/1964 | Forrer |
| 3,133,634 A | 5/1964 | Bozdar |
| 3,173,596 A | 3/1965 | Aust et al. |
| 3,178,242 A | 4/1965 | Ellis et al. |
| 3,228,582 A | 1/1966 | Osberg |
| 3,263,861 A | 8/1966 | Carr |
| 3,265,283 A | 8/1966 | Farquhar |
| 3,300,115 A | 1/1967 | Schauer |
| 3,332,594 A | 7/1967 | De Capua |
| 3,346,167 A | 10/1967 | Schmidt |
| 3,356,279 A | 12/1967 | Root |
| 3,517,858 A | 6/1970 | Farquhar |
| 3,533,549 A | 10/1970 | Gilchrist |
| 3,540,581 A | 11/1970 | Koolnis |
| 3,825,170 A | 7/1974 | Aust et al. |
| 3,904,036 A | 9/1975 | Forrer |
| 4,155,449 A | 5/1979 | Bryne |
| 4,214,660 A | 7/1980 | Hunt, Jr. |
| 4,222,485 A | 9/1980 | Focke |
| 4,256,226 A | 3/1981 | Stone |
| 4,318,474 A | 3/1982 | Hasegawa |
| 4,364,509 A | 12/1982 | Holley, Jr. et al. |
| 4,375,258 A | 3/1983 | Crayne et al. |
| 4,376,509 A | 3/1983 | Schaffer |
| 4,378,877 A | 4/1983 | Botterman et al. |
| 4,396,143 A | 8/1983 | Killy |
| 4,417,655 A | 11/1983 | Forbes, Jr. |
| 4,417,661 A | 11/1983 | Roccaforte |
| 4,538,759 A | 9/1985 | Dutcher |
| 4,577,762 A | 3/1986 | Kuchenbecker |
| 4,588,084 A | 5/1986 | Holley, Jr. |
| 4,605,128 A | 8/1986 | Rieke |
| 4,621,766 A | 11/1986 | McClure |
| 4,658,984 A | 4/1987 | Brunner |
| 4,757,938 A | 7/1988 | Collins |
| 4,817,866 A | 4/1989 | Wonnacott |
| 4,830,267 A | 5/1989 | Wilson |
| 4,890,440 A | 1/1990 | Romagnoli |
| 4,949,845 A | 8/1990 | Dixon |
| 4,967,901 A | 11/1990 | Wood |
| 4,974,771 A | 12/1990 | Lavery |
| 5,072,876 A | 12/1991 | Wilson |
| 5,101,642 A | 4/1992 | Alexandrov |
| 5,119,985 A | 6/1992 | Dawson et al. |
| 5,137,211 A | 8/1992 | Summer et al. |
| 5,219,229 A | 6/1993 | Sengewald |
| 5,249,681 A | 10/1993 | Miller |
| 5,261,594 A | 11/1993 | Brown et al. |
| 5,297,725 A | 3/1994 | Sutherland |
| 5,320,277 A | 6/1994 | Stout et al. |
| 5,333,734 A | 8/1994 | Stout et al. |
| 5,350,109 A | 9/1994 | Brown et al. |
| 5,425,474 A | 6/1995 | Dalea et al. |
| 5,482,185 A | 1/1996 | McNaughton |
| 5,482,203 A | 1/1996 | Stout |
| 5,505,372 A | 4/1996 | Edson et al. |
| 5,577,612 A | 11/1996 | Chesson et al. |
| 5,588,585 A | 12/1996 | McClure |
| 5,597,114 A | 1/1997 | Kramedjian et al. |
| 5,622,309 A | 4/1997 | Matsuda et al. |
| 5,664,683 A | 9/1997 | Brody |
| 5,690,213 A | 11/1997 | Matsumura |
| 5,690,230 A | 11/1997 | Griffith |
| 5,794,778 A | 8/1998 | Harris |
| 5,826,783 A | 10/1998 | Stout |
| 5,873,516 A | 2/1999 | Boggs |
| 5,875,961 A | 3/1999 | Stone et al. |
| 5,881,884 A | 3/1999 | Podosek |
| 5,921,398 A | 7/1999 | Carroll |
| 5,924,559 A | 7/1999 | Carrel et al. |
| 5,927,498 A | 7/1999 | Saam |
| 6,050,402 A | 4/2000 | Walter |
| 6,149,009 A | 11/2000 | Denola |
| 6,170,741 B1 | 1/2001 | Skolik et al. |
| 6,176,419 B1 | 1/2001 | Holley, Jr. |
| 6,250,542 B1 | 6/2001 | Negelen |
| 6,283,293 B1 | 9/2001 | Lingamfelter |
| 6,302,320 B1 | 10/2001 | Stout |
| 6,409,077 B1 | 6/2002 | Telesca et al. |
| D459,927 S | 7/2002 | Flowers et al. |
| 6,471,120 B1 | 10/2002 | Vogel |
| 6,478,219 B1 | 11/2002 | Holley, Jr. |
| 6,484,903 B2 | 11/2002 | Spivey et al. |
| 6,550,615 B2 | 4/2003 | Lingamfelter |
| 6,557,699 B1 | 5/2003 | Focke et al. |
| 6,578,736 B2 | 6/2003 | Spivey |
| 6,604,677 B1 | 8/2003 | Sutherland et al. |
| 6,631,803 B2 | 10/2003 | Rhodes et al. |
| 6,669,083 B2 | 12/2003 | Bates |
| 6,715,639 B2 | 4/2004 | Spivey |
| 6,752,262 B1 | 6/2004 | Boriani et al. |
| 6,766,940 B2 | 7/2004 | Negelen |
| 6,789,673 B2 | 9/2004 | Lingamfelter |
| 6,848,573 B2 | 2/2005 | Gould et al. |
| 6,866,186 B2 | 3/2005 | Fogle et al. |
| 6,902,104 B2 | 6/2005 | Holley, Jr. et al. |
| 6,905,066 B2 | 6/2005 | Holley, Jr. |
| 6,918,487 B2 | 7/2005 | Harrelson |
| 6,926,193 B2 | 8/2005 | Smalley |
| 6,929,172 B2 | 8/2005 | Bates et al. |
| 6,932,265 B2 | 8/2005 | Sax et al. |
| 6,968,992 B2 | 11/2005 | Schuster |
| 6,969,172 B2 | 11/2005 | Actis-Datta |
| 6,974,072 B2 | 12/2005 | Harrelson |
| 6,991,107 B2 | 1/2006 | Harrelson |
| 6,997,316 B2 | 2/2006 | Sutherland |
| 7,000,803 B2 | 2/2006 | Miller |
| 7,073,665 B2 | 7/2006 | Auclair et al. |
| 7,104,435 B2 | 9/2006 | Holley, Jr. |
| 7,134,593 B2 | 11/2006 | Harrelson |
| 7,159,759 B2 | 1/2007 | Sutherland et al. |
| 7,225,930 B2 | 6/2007 | Ford et al. |
| 7,422,104 B2 | 9/2008 | Perkinson |
| 7,478,743 B2 | 1/2009 | Holley, Jr. |
| 7,604,157 B2 | 10/2009 | Zammit et al. |
| 7,699,163 B2 | 4/2010 | Gomes et al. |
| 7,699,215 B2 | 4/2010 | Spivey, Sr. |
| 8,356,743 B2 | 1/2013 | Spivey, Sr. |

(56) References Cited

U.S. PATENT DOCUMENTS

| | | |
|---|---|---|
| 8,387,855 B2 | 3/2013 | Brand |
| 8,439,194 B2 | 5/2013 | Spivey |
| 8,453,919 B2 | 6/2013 | Eckermann |
| 8,496,109 B2 * | 7/2013 | Smalley .............. B65D 5/0227 206/433 |
| 8,919,557 B2 | 12/2014 | Spivey, Sr. |
| 8,955,674 B2 * | 2/2015 | Spivey, Sr. .......... B65D 5/4266 206/148 |
| 8,967,380 B2 | 3/2015 | Moncrief et al. |
| 2001/0017315 A1 | 8/2001 | Baroudi |
| 2002/0029991 A1 | 3/2002 | Lingamfelter |
| 2002/0070139 A1 | 6/2002 | Bates |
| 2002/0088820 A1 | 7/2002 | Spivey |
| 2002/0088821 A1 | 7/2002 | Spivey et al. |
| 2002/0185499 A1 | 12/2002 | Harrelson et al. |
| 2003/0006158 A1 | 1/2003 | Skolik et al. |
| 2003/0136820 A1 | 7/2003 | Negelen |
| 2003/0141313 A1 | 7/2003 | Bates |
| 2003/0150759 A1 | 8/2003 | White, Jr. |
| 2003/0192907 A1 | 10/2003 | Bates |
| 2004/0040334 A1 | 3/2004 | Rusnock |
| 2004/0060972 A1 | 4/2004 | Harrelson |
| 2004/0089575 A1 | 5/2004 | Lingamfelter |
| 2004/0089671 A1 | 5/2004 | Miller |
| 2004/0099558 A1 | 5/2004 | Oliff et al. |
| 2004/0155098 A1 | 8/2004 | Harrelson |
| 2004/0188277 A1 | 9/2004 | Auclair |
| 2004/0188300 A1 | 9/2004 | Sutherland |
| 2004/0188508 A1 | 9/2004 | Holley, Jr. et al. |
| 2005/0023170 A1 | 2/2005 | Lingamfelter |
| 2005/0092820 A1 | 5/2005 | Chekroune |
| 2005/0115843 A1 | 6/2005 | Harrelson |
| 2005/0126947 A1 | 6/2005 | Holley, Jr. |
| 2005/0167291 A1 | 8/2005 | Sutherland |
| 2005/0167478 A1 | 8/2005 | Holley, Jr. |
| 2005/0189405 A1 | 9/2005 | Gomes et al. |
| 2005/0263574 A1 | 12/2005 | Schuster |
| 2006/0054522 A1 | 3/2006 | Kline et al. |
| 2006/0081691 A1 | 4/2006 | Smalley |
| 2006/0091193 A1 | 5/2006 | DeBusk |
| 2006/0118606 A1 | 6/2006 | Holley, Jr. et al. |
| 2006/0131370 A1 | 6/2006 | Bates |
| 2006/0175386 A1 | 8/2006 | Holley, Jr. |
| 2006/0231441 A1 | 10/2006 | Gomes |
| 2006/0231600 A1 | 10/2006 | Holley, Jr. |
| 2006/0249413 A1 | 11/2006 | Auclair et al. |
| 2006/0278689 A1 | 12/2006 | Boshinski et al. |
| 2007/0007325 A1 | 1/2007 | Suzuki et al. |
| 2007/0029371 A1 | 2/2007 | Theelen |
| 2007/0108261 A1 | 5/2007 | Schuster |
| 2007/0131748 A1 | 6/2007 | Brand |
| 2007/0164093 A1 | 7/2007 | Spivey et al. |
| 2007/0181658 A1 | 8/2007 | Sutherland |
| 2007/0205255 A1 | 9/2007 | Dunn |
| 2007/0210144 A1 | 9/2007 | Brand |
| 2007/0251982 A1 | 11/2007 | Brand |
| 2007/0295790 A1 | 12/2007 | Zammit et al. |
| 2008/0023535 A1 | 1/2008 | Holley, Jr. |
| 2008/0048014 A1 | 2/2008 | Bates |
| 2008/0128479 A1 | 6/2008 | Bates et al. |
| 2008/0257944 A1 | 10/2008 | Blin |
| 2009/0282843 A1 | 11/2009 | Brand |
| 2010/0044420 A1 | 2/2010 | Brand et al. |
| 2010/0122999 A1 | 5/2010 | Brand |
| 2010/0237138 A1 | 9/2010 | Bradford |
| 2011/0011924 A1 | 1/2011 | Spivey et al. |
| 2011/0049228 A1 | 3/2011 | Brand |
| 2011/0068160 A1 | 3/2011 | Brand et al. |
| 2011/0290692 A1 * | 12/2011 | Spivey, Sr. ............ B65D 71/36 206/433 |
| 2012/0091021 A1 * | 4/2012 | Smalley ................ B65D 71/36 206/427 |
| 2013/0118942 A1 | 5/2013 | Smalley et al. |
| 2013/0119122 A1 | 5/2013 | Spivey, Sr. |
| 2013/0277260 A1 | 10/2013 | Smalley et al. |
| 2013/0284628 A1 * | 10/2013 | Moncrief ................ B31B 7/00 206/427 |
| 2013/0292285 A1 * | 11/2013 | Kastanek ............... B65D 71/18 206/433 |
| 2014/0260095 A1 * | 9/2014 | Oliveira ................ B65D 71/36 53/410 |

FOREIGN PATENT DOCUMENTS

| | | |
|---|---|---|
| EP | 0 066 029 | 12/1982 |
| EP | 1 433 714 | 6/2004 |
| EP | 1 698 565 | 9/2006 |
| FR | 2 549 010 | 1/1985 |
| GB | 2 264 101 | 8/1993 |
| JP | 2002-128064 | 5/2002 |
| JP | 2005-255224 A | 9/2005 |
| JP | 2006-111342 | 4/2006 |
| JP | 2007-055630 | 3/2007 |
| JP | 2007-532421 | 11/2007 |
| JP | 2010-149927 | 7/2010 |
| KR | 10-0154124 | 2/1999 |
| KR | 10-0371048 | 8/2003 |
| WO | WO 96/21603 | 7/1996 |
| WO | WO 96/29260 | 9/1996 |
| WO | WO 99/28198 | 6/1999 |
| WO | WO 99/64301 | 12/1999 |
| WO | WO 00/03937 | 1/2000 |
| WO | WO 02/47990 | 6/2002 |
| WO | WO 2004/043790 | 5/2004 |
| WO | WO 2005/051781 | 6/2005 |
| WO | WO 2005/100175 | 10/2005 |
| WO | WO 2006/050210 | 5/2006 |
| WO | WO 2006/050316 | 5/2006 |
| WO | WO 2007/076544 | 7/2007 |

OTHER PUBLICATIONS

International Search Report and Written Opinion for PCT/US2014/037640 dated Sep. 12, 2014.

International Search Report and Written Opinion for PCT/US2014/037655 dated Sep. 4, 2014.

International Search Report and Written Opinion for PCT/US2014/037656 dated Sep. 4, 2014.

International Search Report and Written Opinion for PCT/US2014/069472 dated Apr. 1, 2015.

* cited by examiner

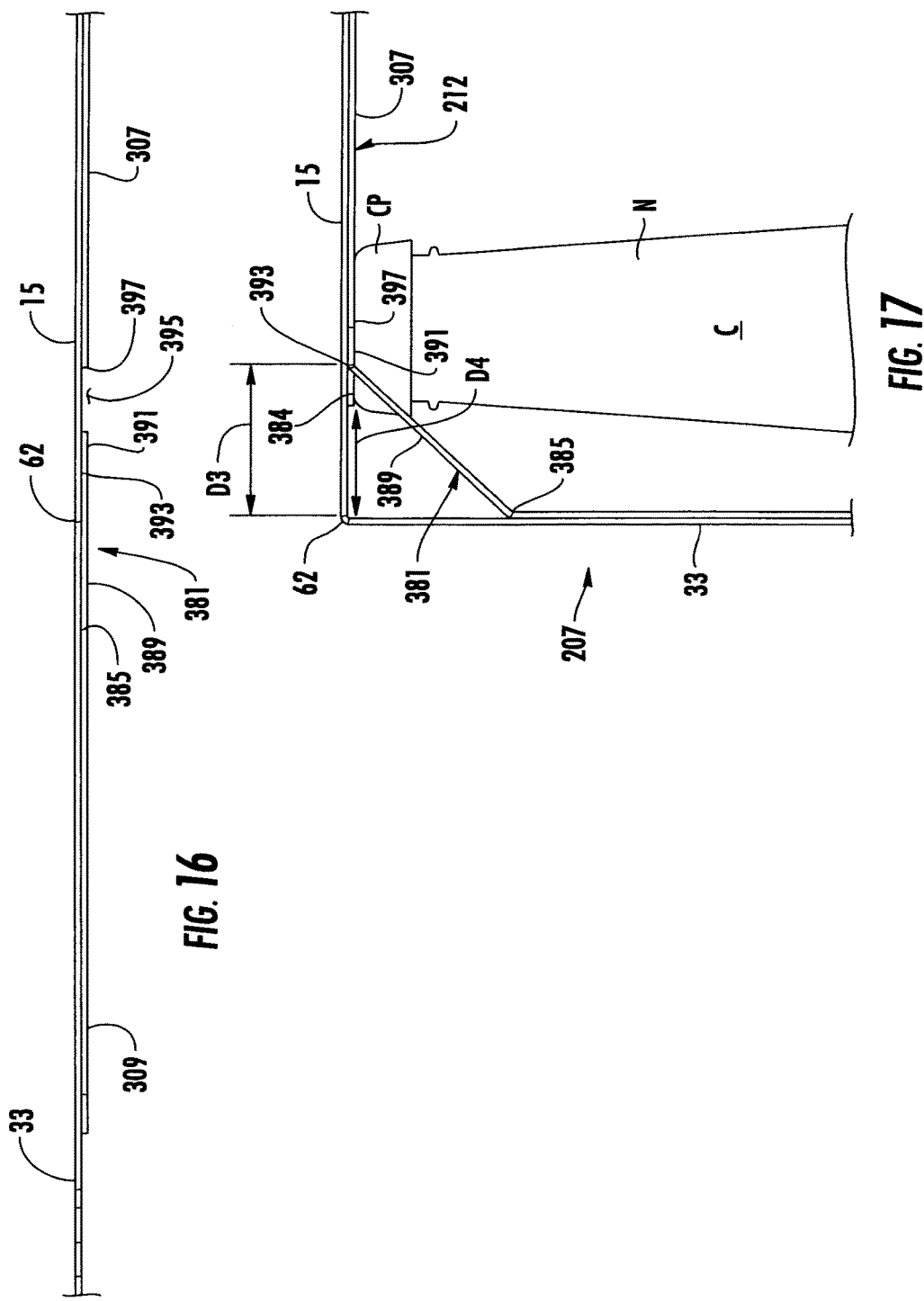

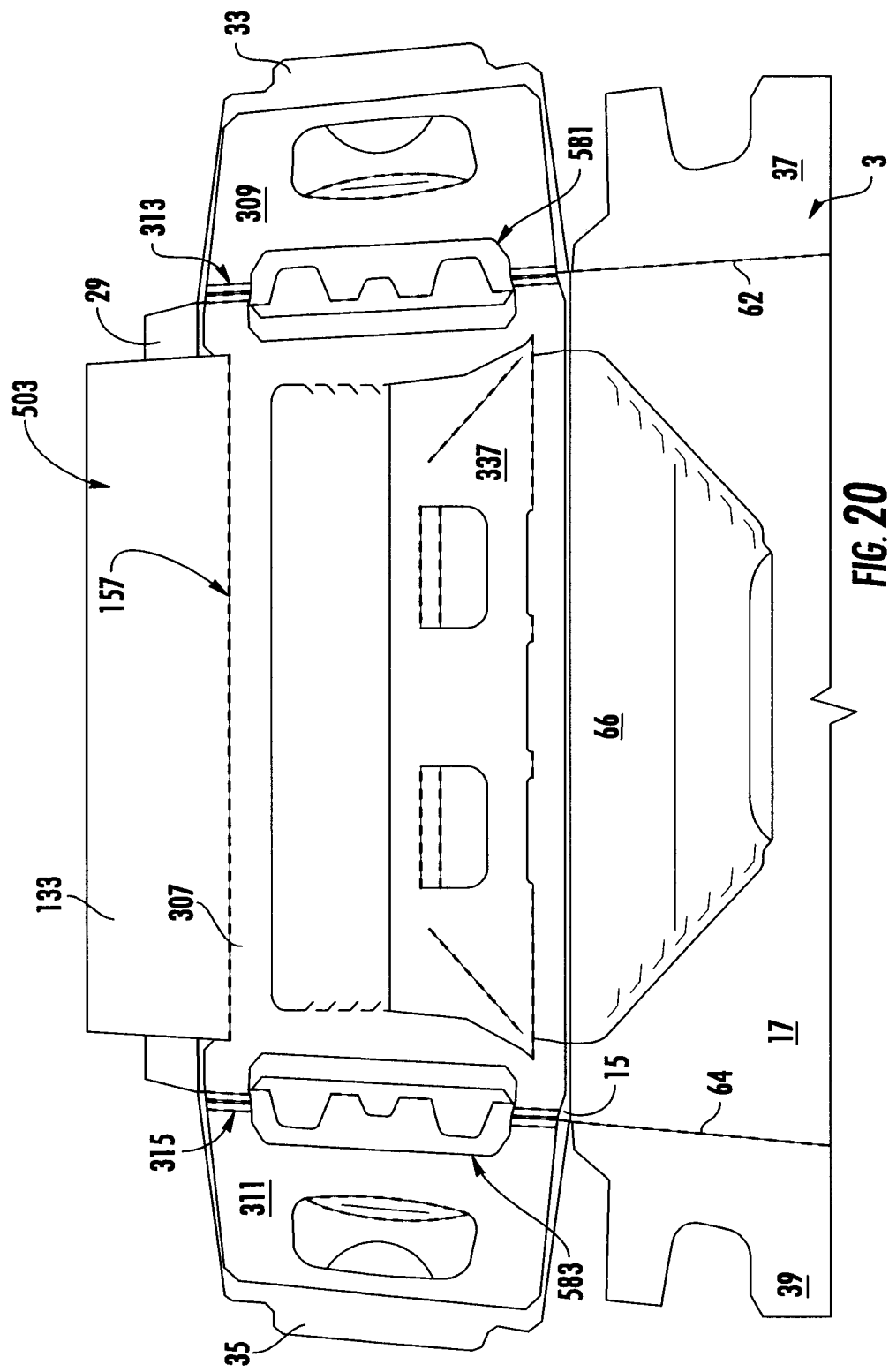

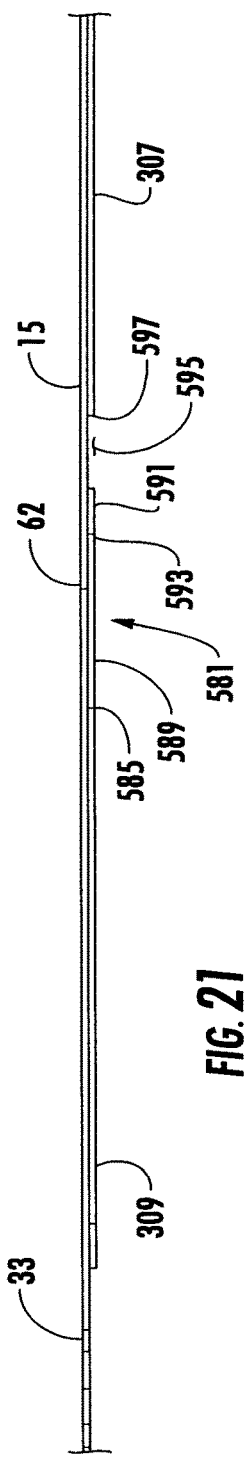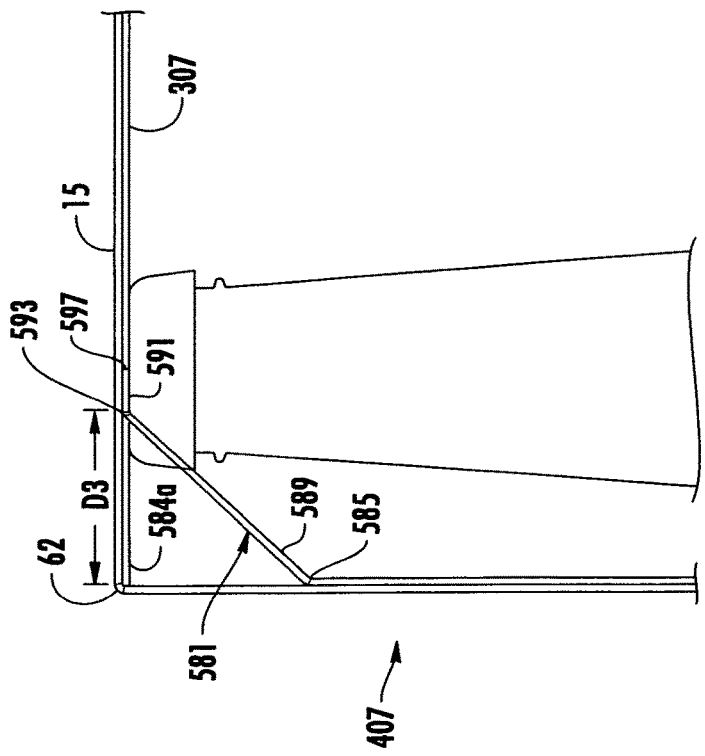

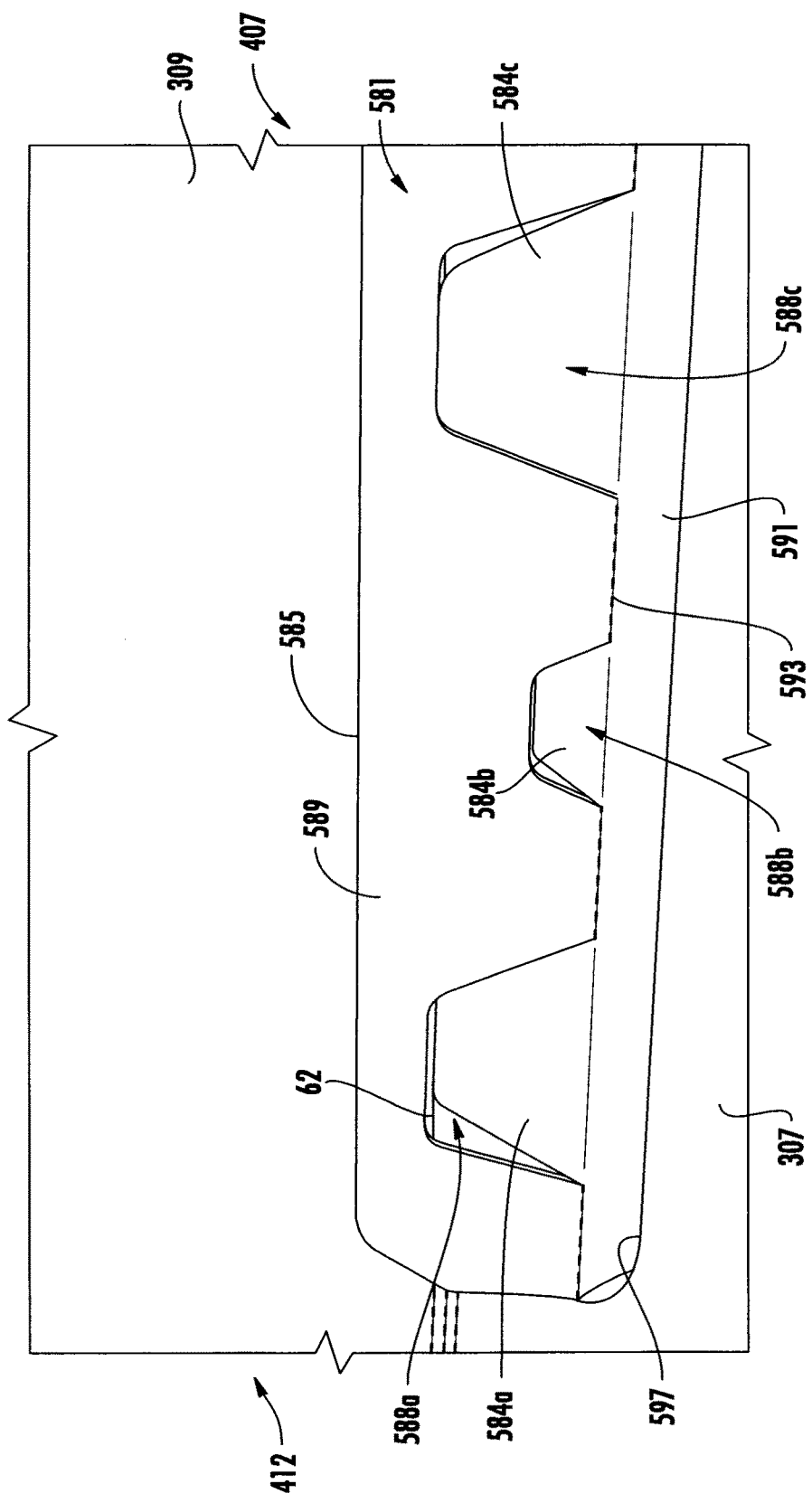

CARTON WITH ARTICLE PROTECTION FEATURES

CROSS REFERENCE TO RELATED APPLICATIONS

This application claims the benefit of U.S. Provisional Patent Application No. 61/963,653, filed Dec. 10, 2013, and U.S. Provisional Patent Application No. 61/966,736, filed Feb. 28, 2014.

INCORPORATION BY REFERENCE

The disclosures of U.S. Provisional Patent Application No. 61/855,323, which was filed on May 13, 2013, U.S. Provisional Patent Application No. 61/855,305, which was filed on May 13, 2013, U.S. Provisional Patent Application No. 61/959,162, which was filed on Aug. 16, 2013, U.S. Provisional Patent Application No. 61/963,653, which was filed on Dec. 10, 2013, U.S. Provisional Patent Application No. 61/966,736, which was filed on Feb. 28, 2014, U.S. patent application Ser. No. 14/274,975, which was filed on May 12, 2014, U.S. patent application Ser. No. 14/275,143, which was filed on May 12, 2014, U.S. patent application Ser. No. 13/419,740, which was filed on Mar. 14, 2012, U.S. patent application Ser. No. 13/768,079, which was filed on Feb. 15, 2013, and U.S. patent application Ser. No. 13/833,542, which was filed on Mar. 15, 2013, are hereby incorporated by reference for all purposes as if presented herein in their entirety.

BACKGROUND OF THE DISCLOSURE

The present disclosure generally relates to cartons for holding beverage containers or other types of articles. More specifically, the present disclosure relates to cartons having article protection features.

SUMMARY OF THE DISCLOSURE

In general, one aspect of the disclosure is directed to a carton for holding a plurality of containers. The carton can comprise a plurality of panels that extends at least partially around an interior of the carton. The plurality of panels comprises a top panel. An insert can comprise a central panel, an inner end flap foldably connected to the central panel, and at least one crown guard flap foldably connected to the inner end flap adjacent a crown guard opening in the insert. The central panel can comprise a stop edge adjacent the crown guard opening, and the crown guard flap can comprise a first portion foldably connected to the inner end flap and a second portion foldably connected to the first portion. The top panel can at least partially overlap the central panel, and the second portion of the crown guard flap can be disposed adjacent the stop edge of the central panel.

In another aspect, the disclosure is generally directed to, in combination, a carton blank and an insert blank for forming a carton for holding a plurality of containers. The carton blank can comprise a plurality of panels comprising a top panel. The insert blank can comprise a central panel, an inner end flap foldably connected to the central panel, and at least one crown guard flap foldably connected to the inner end flap adjacent a crown guard opening in the insert. The central panel can comprising a stop edge adjacent the crown guard opening, and the crown guard flap can comprise a first portion foldably connected to the inner end flap and a second portion foldably connected to the first portion. The top panel can at least partially overlap the central panel, and the second portion of the crown guard flap can be spaced apart from the stop edge of the central panel by the crown guard opening.

In another aspect, the disclosure is generally directed to a method of forming a carton for holding a plurality of containers. The method can comprise obtaining a carton blank comprising a plurality of panels comprising a top panel, and obtaining an insert blank comprising a central panel, an inner end flap foldably connected to the central panel, and at least one crown guard flap foldably connected to the inner end flap adjacent a crown guard opening in the insert. The central panel can comprise a stop edge adjacent the crown guard opening, and the crown guard flap can comprise a first portion foldably connected to the inner end flap and a second portion foldably connected to the first portion. The second portion can be spaced apart from the stop edge of the central panel by the crown guard opening. The method further can comprise positioning the insert blank relative to the carton blank so that the top panel at least partially overlaps the central panel, and forming an interior of the carton at least partially defined by the plurality of panels. The forming the interior of the carton can comprise forming an open-ended sleeve. Further, the method can comprise forming a crown retention feature in the interior of the carton comprising folding the inner end flap over an end of the open-ended sleeve, the folding the inner end flap causing the first portion of the crown guard flap to fold with respect to the inner end flap and the second portion of the crown guard flap and positioning the second portion to be adjacent the stop edge of the central panel.

Those skilled in the art will appreciate the above stated advantages and other advantages and benefits of various additional embodiments reading the following detailed description of the embodiments with reference to the below-listed drawing figures. It is within the scope of the present disclosure that the above-discussed aspects be provided both individually and in various combinations.

BRIEF DESCRIPTION OF THE DRAWINGS

According to common practice, the various features of the drawings discussed below are not necessarily drawn to scale. Dimensions of various features and elements in the drawings may be expanded or reduced to more clearly illustrate the embodiments of the disclosure.

FIGS. 16 and 17 are schematic side views of an open-ended sleeve formed from the combination of FIG. 15 and showing the formation of a crown retention feature according to the second exemplary embodiment of the disclosure.

FIG. 20 is a plan view of the insert blank of FIG. 19 in combination with the carton blank of FIG. 1.

FIGS. 21 and 22 are schematic side views of an open-ended sleeve formed from the combination of FIG. 20 and showing the formation of a crown retention feature according to the third exemplary embodiment of the disclosure.

FIG. 23 is an interior perspective view showing the configuration of the crown guard feature of FIG. 22.

Corresponding parts are designated by corresponding reference numbers throughout the drawings.

DETAILED DESCRIPTION OF THE EXEMPLARY EMBODIMENTS

The present disclosure generally relates to cartons that contain articles such as containers, bottles, cans, etc. The articles can be used for packaging food and beverage products, for example. The articles can be made from materials suitable in composition for packaging the particular food or beverage item, and the materials include, but are not limited to, aluminum and/or other metals; glass; plastics such as PET, LDPE, LLDPE, HDPE, PP, PS, PVC, EVOH, and Nylon; and the like, or any combination thereof.

Cartons according to the present disclosure can accommodate articles of any shape. For the purpose of illustration and not for the purpose of limiting the scope of the disclosure, the following detailed description describes beverage containers (e.g., glass beverage bottles) as disposed within the carton embodiments. In this specification, the terms "inner," "interior," "outer," "exterior," "lower," "bottom," "upper," and "top" indicate orientations determined in relation to fully erected and upright cartons.

Figure 1:
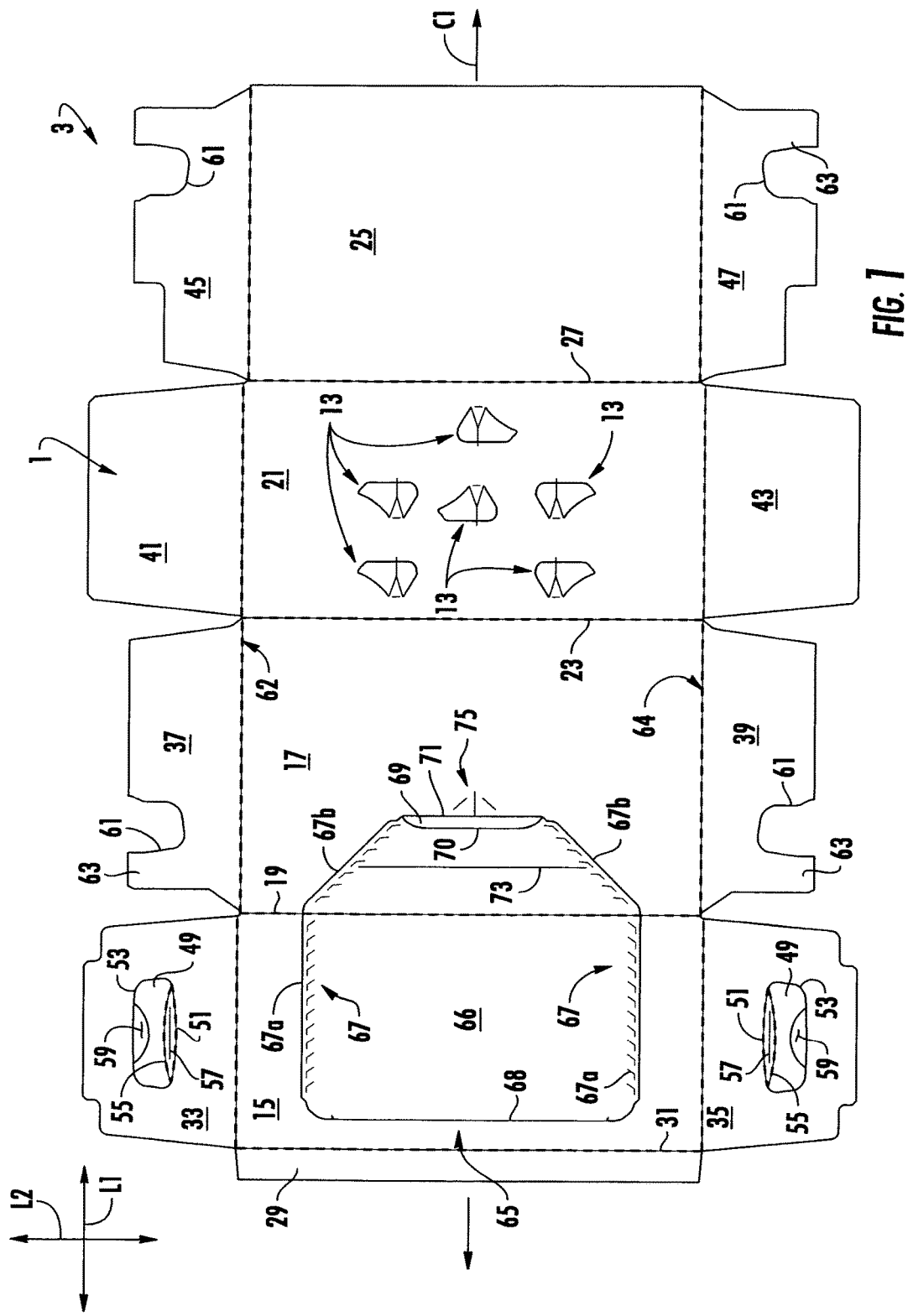
FIG. 1 is a plan view of an interior surface of a blank for forming a carton according to a first exemplary embodiment of the disclosure.

FIG. 1 is a plan view of the interior side 1 of a blank, generally indicated at 3, used to form a carton 5 (FIG. 13) according to a first exemplary embodiment of the disclosure. The carton 5 can be used to house a plurality of articles such as containers C with necks or upper portions N that are generally narrower than the lower portions of the containers (FIG. 8-11). The containers C can include tops or caps CP (FIG. 8-11). In the illustrated embodiment, the carton 5 is sized to house eighteen containers C in a single layer in a 3×6 arrangement, but it is understood that the carton 5 may be sized and shaped to hold containers of a different or same quantity in more than one layer and/or in different row/column arrangements (e.g., 1×6, 3×4, 2×6×2, 3×5, 4×5, 2×9, 2×6, 4×4, etc.). The carton 5 can include a dispenser 10 (FIG. 13) for allowing access to the containers C. In the illustrated embodiment, the carton 5 includes first and second handles 11 (FIGS. 12 and 13) for grasping and carrying the carton at a respective first end 7 and second end 9 of the carton. As will be discussed below in more detail, the handles 11, are formed from various features in the blank 3. The carton 5 includes an insert 12 (FIGS. 6-12) that reinforces and strengthens the handles 11 and includes crown guard features (e.g., a crown retention panel, an inner side flap, and crown guard flaps) that reinforce and stabilize the containers C in the carton.

The blank 3 and carton 5 can have features that are similar or identical to the features described in any of the embodiments disclosed in the above-noted incorporated by reference patent applications, including U.S. patent application Ser. No. 13/419,740, and all related applications. Accordingly, in one embodiment, the carton 5 may have article protection flaps 13 for protecting the at least one article. As noted in the incorporated by reference applications, the article protection flaps 13 are moveable between a first position and a second position placed between adjacent containers C in the carton to reduce movement of the containers in the carton and prevent breakage of the containers. The carton 5 can have other features (e.g., article protection features in the ends 7, 9 of the carton 5 for cushioning one or more of the containers C) without departing from the disclosure.

The carton blank 3 has a longitudinal axis L1 and a lateral axis L2. The carton blank 3 can include a longitudinal centerline C1, as shown in FIG. 1. In the illustrated embodiment, the blank 3 comprises a top panel 15 foldably connected to a first side panel 17 at a first lateral fold line 19. A bottom panel 21 is foldably connected to the first side panel 17 at a second lateral fold line 23. A second side panel 25 is foldably connected to the bottom panel 21 at a third lateral fold line 27. In the illustrated embodiment, the blank 3 includes an attachment flap 29 foldably connected to the top panel 15 at a fourth lateral fold line 31. Any of the top and bottom panels 15, 21, the first and second side panels 17, 25, and the attachment flap 29 can be otherwise shaped, arranged, configured, or omitted, without departing from the disclosure. For example, the blank 3 can alternatively include two top panels cooperating to form a top of the carton 5 or two bottom panels cooperating to form a bottom of the carton. Additionally, the attachment flap 29 could be foldably connected to the second side panel 25 in an alternative embodiment.

The top panel 15 is foldably connected to a first top end flap 33 and a second top end flap 35. The first side panel 17 is foldably connected to a first side end flap 37 and a second side end flap 39. The bottom panel 21 is foldably connected to a first bottom end flap 41 and a second bottom end flap 43. The second side panel 25 is foldably connected to a first side end flap 45 and a second side end flap 47. When the carton 5 is erected, the top and bottom end flaps 33 and 41 and side end flaps 37 and 45 close the first end 7 of the carton, and the top and bottom end flaps 35 and 43 and side end flaps 39 and 47 close the second end 9 of the carton. In accordance with an alternative embodiment of the present disclosure, different flap arrangements can be used for at least partially closing the ends 7, 9 of the carton 5.

In one embodiment, the top and bottom end flaps 33 and 41 and side end flaps 37 and 45 extend along a first marginal area of the blank 3, and are foldably connected at a first longitudinal fold line 62 that extends along the length of the blank. In the illustrated embodiment, the top and bottom end flaps 35 and 43 and side end flaps 39 and 47 extend along a second marginal area of the blank 3, and are foldably connected at a second longitudinal fold line 64 that also extends along the length of the blank. The longitudinal fold lines 62, 64 may be, for example, substantially straight, or offset at one or more locations to account for blank thickness or for other factors.

As shown in FIG. 1, the features that form the handles 11 of the carton 5 include elongate handle flaps 49 formed in respective top end flaps 33, 35 and foldably attached to the respective top end flap at a respective arcuate fold line 51. The handle flaps 49 are separable from the respective top end flaps 33, 35 along a respective cut or tear line 53. An opposing arcuate fold line 55 can extend in each of the handle flaps 49 adjacent or proximate the respective arcuate fold lines 51, and a longitudinal score 57 can extend between the opposing arcuate fold lines 51, 55 in each of the handle flaps. In one embodiment, each of the handle flaps 49 can have an edge (e.g., a curved edge) that is adjacent a cutout 59. The features that form the handles 11 further include cutouts 61 in the respective side end flaps 37, 45, 39, 47. The side end flaps 37, 45, 39, 47 can also include respective upper portions 63 disposed above the respective cutouts 61. One of the handles 11 could have different features than the other handle or could be omitted without departing from the disclosure. One or both of the handles 11 could be otherwise shaped, arranged, and/or configured without departing from the disclosure. For example, one or both of the opposing arcuate fold lines 51, 55 in each handle 11 could be generally longitudinal.

According to the illustrated embodiment, the dispenser 10 comprises an outer dispenser pattern 65 including an outer dispenser panel 66, two outer tear lines 67, and a fold line 68 in the carton blank 3. The outer dispenser panel 66 is defined by the fold line 68 extending in the top panel 15 generally in the lateral L2 direction and the outer tear lines 67, which extend from the respective ends of the fold line 68 in the top panel 15 and into the first side panel 17. As shown in FIG. 1, each of the tear lines 67 can include a generally longitudinal portion 67a in at least the top panel 15 and an oblique portion 67b in at least the first side panel 17. In the illustrated embodiment, the outer dispenser pattern 65 can include an access panel 69 that is foldably connected to the outer dispenser panel 66 along a lateral fold line 70 and is separable from the outer dispenser panel 66 and the first side panel 17 along a tear or cut line 71. The outer dispenser panel 66 is separable from the top panel along the outer tear lines 67 to form a dispenser opening (not shown) to provide access to the containers C within the carton. The access panel 69 can help initiate tearing along the outer tear lines 67 by folding inwardly along the fold line 70 to form an access opening capable of receiving a hand, fingers, etc. so that a user can grip the outer dispenser panel 66 adjacent the access panel 69 and pull the outer dispenser panel 66 outwardly from the carton 5. As shown in FIG. 1, the outer dispenser pattern 65 can also include a lateral score 73 and cuts 75 that can also help with actuating the outer dispenser panel 66. The outer dispenser pattern 65 could be omitted or could be otherwise shaped, arranged, positioned and/or configured without departing from the disclosure.

In the illustrated embodiment, the bottom panel 21 includes six article protection flaps 13 foldably connected to the bottom panel and arranged in three rows with the middle row offset from the outer rows and with the article protection flaps 13 having different orientations. In the illustrated embodiment, the article protection flaps 13 are asymmetric. The article protection flaps 13 could be omitted or could be otherwise shaped, arranged, positioned, and/or configured without departing from the disclosure. For example, the article protection flaps can be similar to, or the same as, those described in U.S. patent application Ser. No. 13/419,740, filed Mar. 14, 2012, the disclosure of which is hereby incorporated by reference for all purposes as if presented herein in its entirety.

Figure 2:
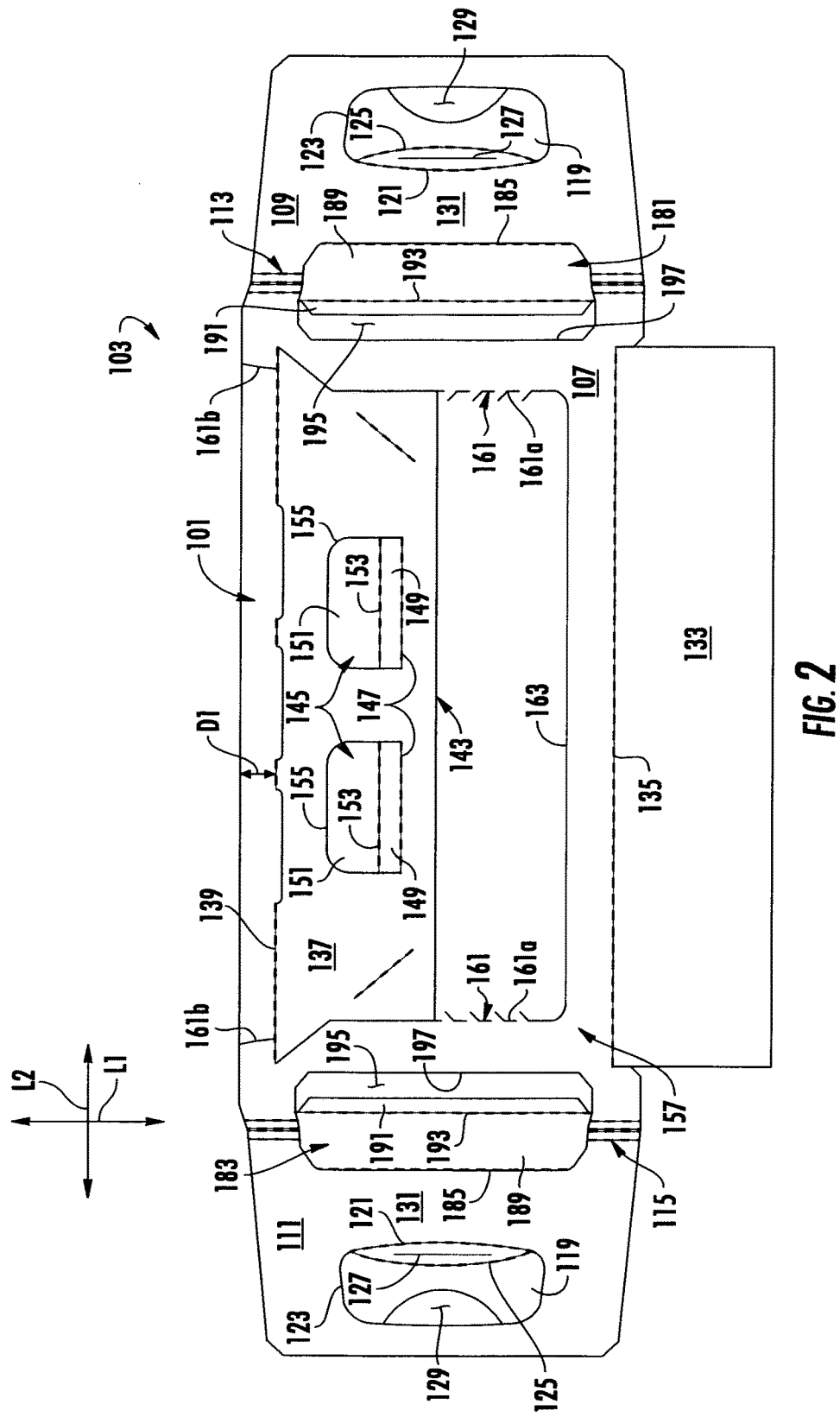
FIG. 2 is a plan view of an insert blank for forming an insert according to the first exemplary embodiment of the disclosure.
Figure 3:
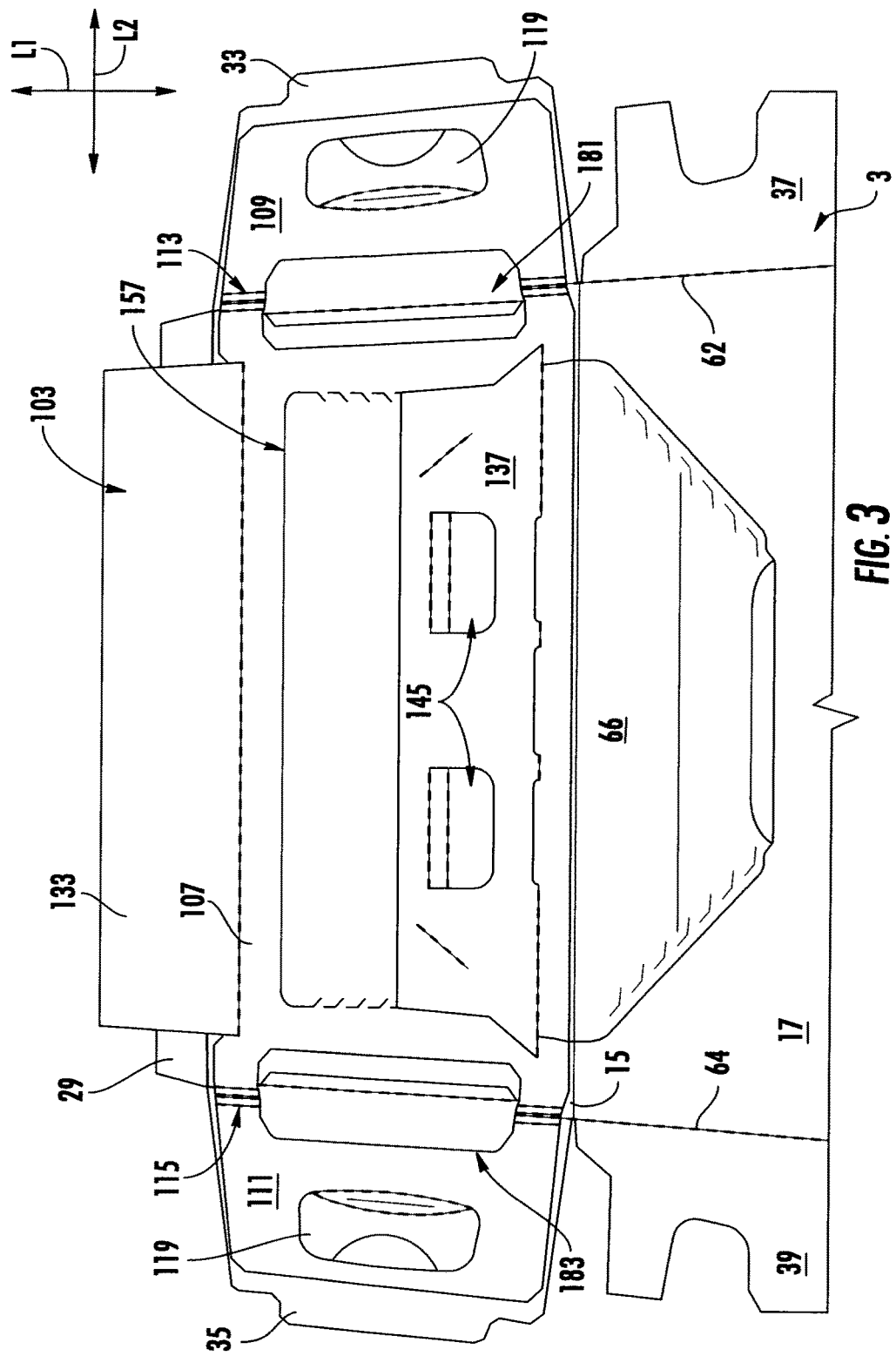
FIGS. 3 and 4 are plan views of the insert blank of FIG. 2 in combination with the carton blank of FIG. 1.

FIG. 2 illustrates an exterior surface 101 of an insert blank 103 used to form the insert 12 (FIGS. 6-12) for use in the carton 5 according to the exemplary embodiment of the disclosure. As illustrated in FIGS. 2 and 3, the longitudinal axis L1 and the lateral axis L2 of the insert blank 103 are oriented so that the longitudinal axis L1 and the lateral axis L2 of the insert blank 103 comport with the respective longitudinal axis L1 and lateral axis L2 of the carton blank 3 established in FIG. 1. In the illustrated embodiment, the insert blank 103 includes a central panel 107 and two inner end flaps 109, 111 respectively foldably connected to the central panel 107 at opposite ends of the central panel. A first fold line or area 113 connects the first inner end flap 109 to the central panel 107 at the first end of the insert blank 103, and a second fold line or area 115 connects the second inner end flap 111 to the central panel 107 at the second end of the insert blank 103. In the illustrated embodiment, each of the fold areas 113, 115 can include several fold lines (e.g., scores, creases, cut-crease lines, etc.). Alternatively, the fold areas 113, 115 can be other lines or areas of weakening for folding the reinforcing end panels 109, 111 relative to the central panel 107 (e.g., a single fold line).

In the illustrated embodiment, the insert blank 103 includes features for forming the handles 11 in the carton 5. Each of the inner end flaps 109, 111 can include an inner handle flap 119 foldably attached to the respective inner end flap at a respective arcuate fold line 121. The inner handle flaps 119 are separable from the respective inner end flaps 109, 111 along a respective cut or tear line 123. An opposing arcuate fold line 125 can extend in each of the inner handle flaps 119 adjacent or proximate the respective arcuate fold lines 121, and a longitudinal fold line 127 can extend between the opposing arcuate fold lines 121, 125 in each of the inner handle flaps. In one embodiment, each of the inner handle flaps 119 can have an edge (e.g., a curved edge) that is adjacent a cutout 129. An upper portion 131 can be disposed above each of the inner handle flaps 119 in each of the inner end flaps 109, 111. The inner handle flaps 119, the fold lines 121, 125, 127, and the cutouts 129 can be similar or identical to the respective outer handle flaps 49, fold lines 51, 55, 57, and cutouts 59 so that the inner and outer handle flaps, fold lines, and cutouts are generally aligned and/or are overlapped with respect to one another in the handles 11 in the erected carton 5. The inner handle flaps 119, the fold lines 121, 125, 127, the cutouts 129, the outer handle flaps 49, the fold lines 51, 55, 57, and/or the cutouts 59 could be otherwise shaped, arranged, and/or configured without departing from the disclosure. For example, one or both of the opposing arcuate fold lines 121, 125 in each of the inner handle flaps 119 could be generally longitudinal.

In the illustrated embodiment, the insert blank 103 includes a side flap 133 foldably connected to the central panel 107 at a lateral fold line 135, which, as shown in FIG. 2, is offset from the outer edge of the insert blank 103. In one embodiment, an inner side panel or crown retention panel 137 can be included in the central panel 107. As shown in FIG. 2, the crown retention panel 137 is foldably connected to the central panel 107 along a lateral fold line 139 that is spaced apart from a free edge 141 of the insert blank 103 by a distance D1. The crown retention panel 137 can be separable from the central panel 107 along a tear or cut line 143. As shown in FIG. 2, the cut line 143 includes oblique portions extending from the fold line 139 and longitudinal portions extending from the oblique portions to a lateral portion. In the illustrated embodiment, the crown retention panel 137 includes two attachment flaps 145 foldably connected to the crown retention panel 137 along lateral fold lines 147. Each of the attachment flaps 145 can include a proximal portion 149 foldably connected to a distal portion 151 along a lateral fold line 153 so that the proximal portion 149 can be independently positioned with respect to the distal portion 151. In one embodiment, each of the attachment flaps 145 can be separable from the crown retention panel 137 along a respective tear or cut line 155 (e.g., a U-shaped cut line). The side flap 133, the crown retention panel 137, and/or the attachment flaps 145 could be otherwise shaped, arranged, and/or configured without departing from the disclosure. For example, the crown retention panel 137 could include any suitable number of attachment flaps 145 (e.g., one or more than two attachment flaps). Additionally, one or both of the attachment flaps 145 and/or the crown retention panel 137 could be rotated with respect to the orientation shown in FIG. 2.

As shown in FIG. 2, the insert blank 103 can include an inner dispenser pattern 157 including an inner dispenser portion 159 (e.g., an inner dispenser panel) at least partially defined by inner tear lines 161. Each of the inner tear lines 161 can include a first portion 161a extending from the cut or tear line 143 towards the fold line 135 and a second portion 161b extending from the free edge 141 of the insert blank 103 to the fold line 139. In one embodiment, the portions 161a of the tear line 161 are generally aligned with the respective longitudinal portions of the cut line 143. As shown in FIG. 2, the inner dispenser panel 159 can be foldably connected to the central panel 107 along a lateral fold line 163 extending between the ends of the portions 161a of the tear lines 161. The inner dispenser portion 159 is configured to be aligned with the outer dispenser panel 66 of the top panel 15 of the carton blank 3. In one embodiment, the inner dispenser panel 159 can include at least a portion of the crown retention panel 137. For example, the crown retention panel 137 can be pivoted upwardly with the dispenser panels 66, 159 when the dispenser is actuated. The inner dispenser pattern 157 could be otherwise shaped, arranged, positioned, and/or configured without departing from the disclosure.

In the illustrated embodiment, the insert blank 103 includes crown guard flaps 181, 183 foldably connected to the respective inner end flaps 109, 111. As shown in FIG. 37, each of the crown guard flaps 181, 183 includes a first portion 189 (e.g., a proximal portion) foldably connected to the respective inner end flap 109, 111 along a respective fold line 185 and a second portion 191 (e.g., a distal portion) foldably connected to the respective first portion 189 along a respective fold line 193. The crown guard flaps 181 can extend in a respective opening or crown guard relief 195 in the central panel 107 and the respective inner end flap 109, 111, interrupting the respective fold areas 113, 115. Accordingly, each of the fold areas 113, 115 includes two segments, each extending from the respective crown guard reliefs 195 to the outer edge of the insert 103. The central panel 107 can include a stop edge 197 in each of the crown guard reliefs 195, and the stop edges 197 can be sized and shaped to receive the respective second portions 191 of the respective crown guard flaps 181. The inner end flaps 109, 111 and/or the crown guard flaps 181, 183 could be otherwise shaped, arranged, and/or configured without departing from the disclosure. Further, any of the inner end flaps 109, 111 and/or the crown guard flaps 181, 183 could be omitted without departing from the disclosure.

Figure 4:
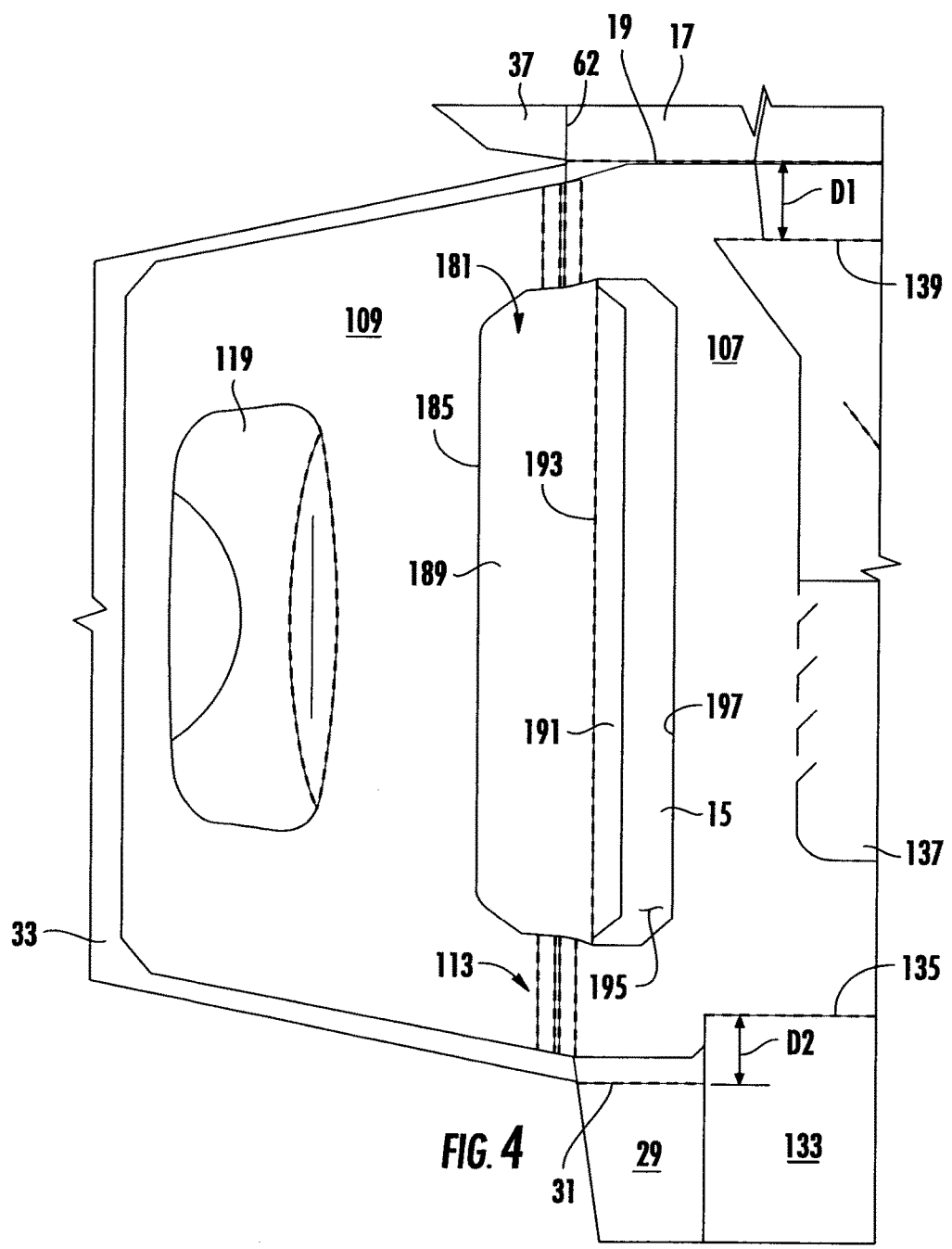

As shown in FIGS. 3-7, in one exemplary embodiment, the carton 5 can be assembled by initially adhering the insert blank 103 to the top panel 15 and the top flaps 33, 35 of the carton blank 3. In the illustrated embodiment, the insert blank 103 can be positioned on the interior surface of the carton blank 3 so that the central panel 107 is at least partially in face-to-face contact with the top panel 15 and the inner end flaps 109, 111 are at least partially in face-to-face contact with the respective top end flaps 33, 35 with the fold areas 113, 115 generally aligned with the respective longitudinal fold lines 62, 64 (FIGS. 3 and 4). Additionally, the crown guard flaps 181, 183 can be overlapped by the top panel 15, the respective top end flaps 33, 35, and the respective fold lines 62, 64 (FIGS. 3 and 4). For example, the relationship between the crown guard flap 181 and the crown guard relief 195 with the top panel 15, the top end flap 33, the fold line 62, the central panel 107, and the inner end flap 109 is shown in the schematic cross-sectional view of FIG. 7. In the illustrated embodiment, the insert blank 103 can be positioned so that the lateral fold line 135 connecting the side flap 133 to the central panel 107 is spaced apart from the lateral fold line 31 connecting the top panel 15 to the attachment flap 29 by at least a distance D2 (FIG. 4) and the lateral fold line 139 connecting the crown retention panel 137 to the central panel 107 is spaced apart from the lateral fold line 19 and the first side panel 17 by at least the distance D1 (FIGS. 2 and 4). The insert blank 103 could be otherwise positioned on the carton blank 3 without departing from the scope of this disclosure.

In the illustrated embodiment, the central panel 107 can be glued to the interior surface of the top panel 15, and the inner end flaps 109, 111 can be glued to the respective top end flaps 33, 35, such as by glue strips (not shown). In one embodiment, the crown retention panel 137 is not glued to the top panel 15, the side flap 133 is not glued to the top panel 15 or the attachment flap 29, and the crown guard flaps 181, 183 are not glued to the top panel 15 or the top end flaps 33, 35 so that the crown retention panel 137, the side flap 133, and the crown guard flaps 181, 183 can be positioned independently of the side panels, the attachment flap, and the top panel, and the top end flaps. In the illustrated embodiment, when the insert blank 103 is glued to the carton blank 3, the outer handle flaps 49 at least partially overlap and/or are generally aligned with the inner handle flaps 119.

In the illustrated embodiment, the carton blank 103 can be folded along the lateral fold lines 19 and 27 so that the first side panel 17 generally overlaps the top panel 15 and the central panel 107 and so that the second side panel 25 generally overlaps the attachment flap 29. The attachment flap 29 can be glued to the interior surface of the second side panel 25, such as by a glue strip (not shown). Similarly, the attachment flaps 145 of the crown retention panel 137 can be glued to the first side panel 17, such as by respective glue strips (not shown). In one embodiment, the attachment flaps 145 can be glued to the portion of the dispenser panel 66 that extends in the first side panel 17.

Figure 5:
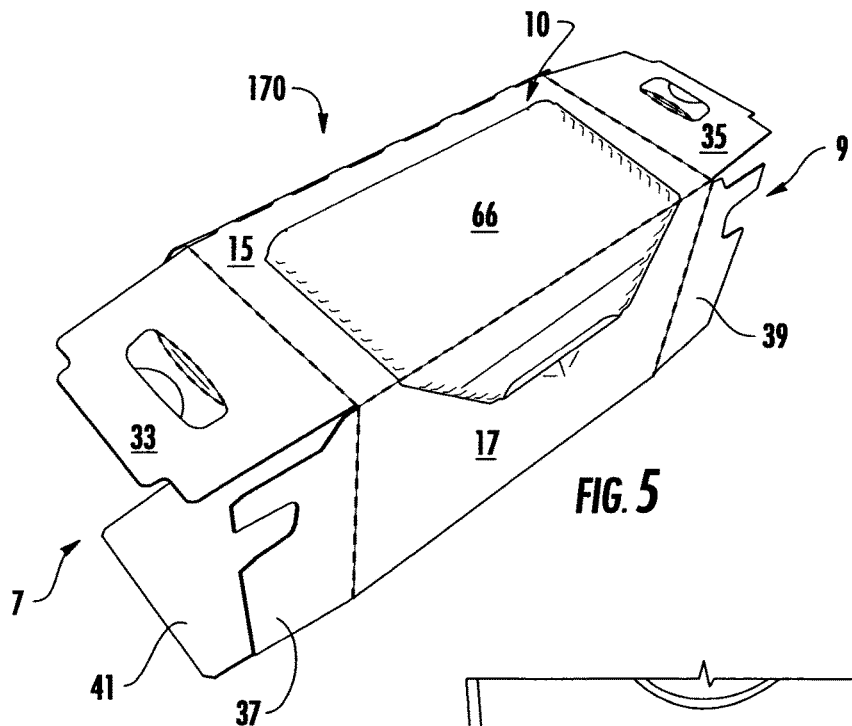
FIG. 5 is an external perspective view of an open-ended sleeve formed by the combination of FIGS. 3 and 4 according to the first exemplary embodiment of the disclosure.
Figure 6:
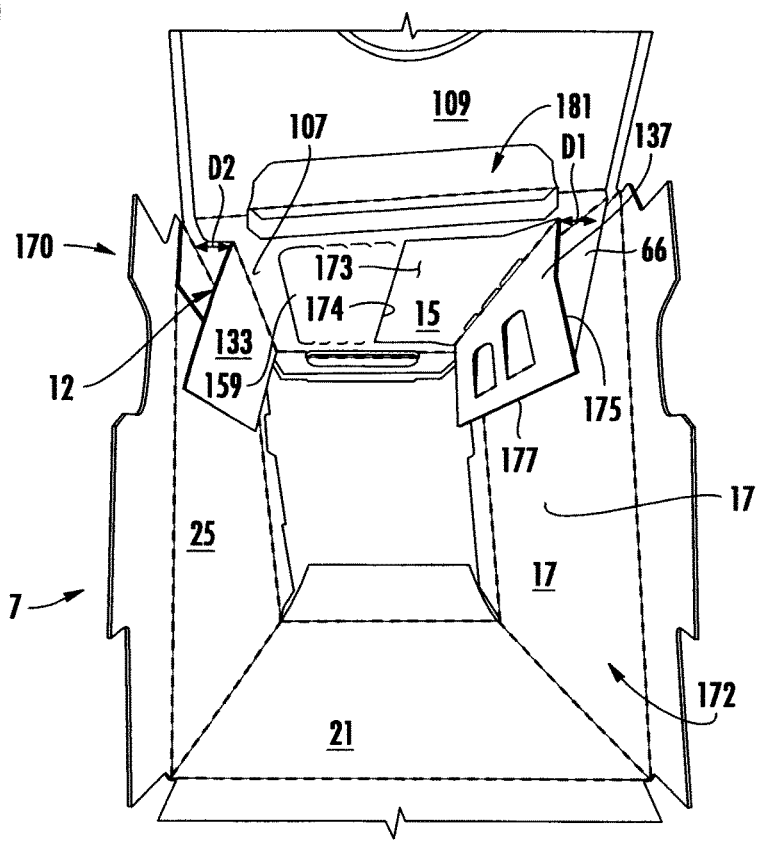
FIG. 6 is an internal perspective view of the open-ended sleeve of FIG. 5.
Figure 10:
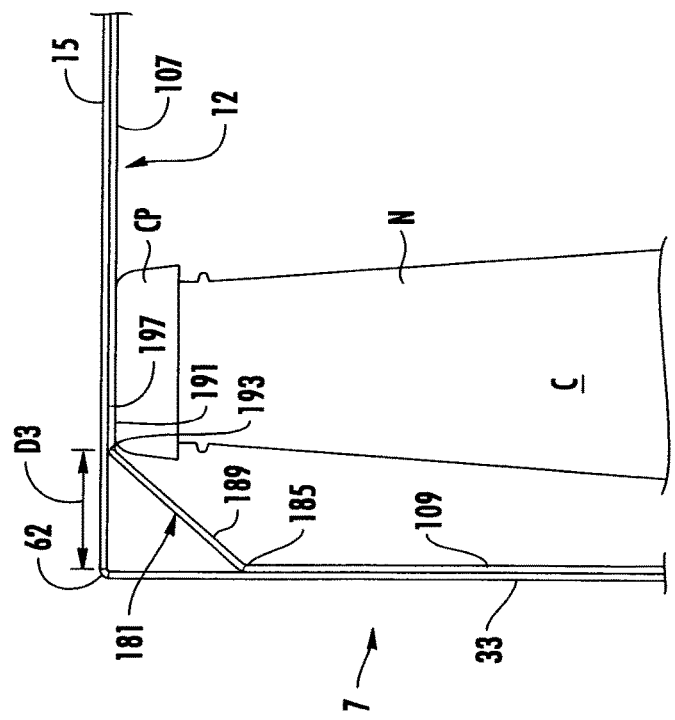
Figure 8:
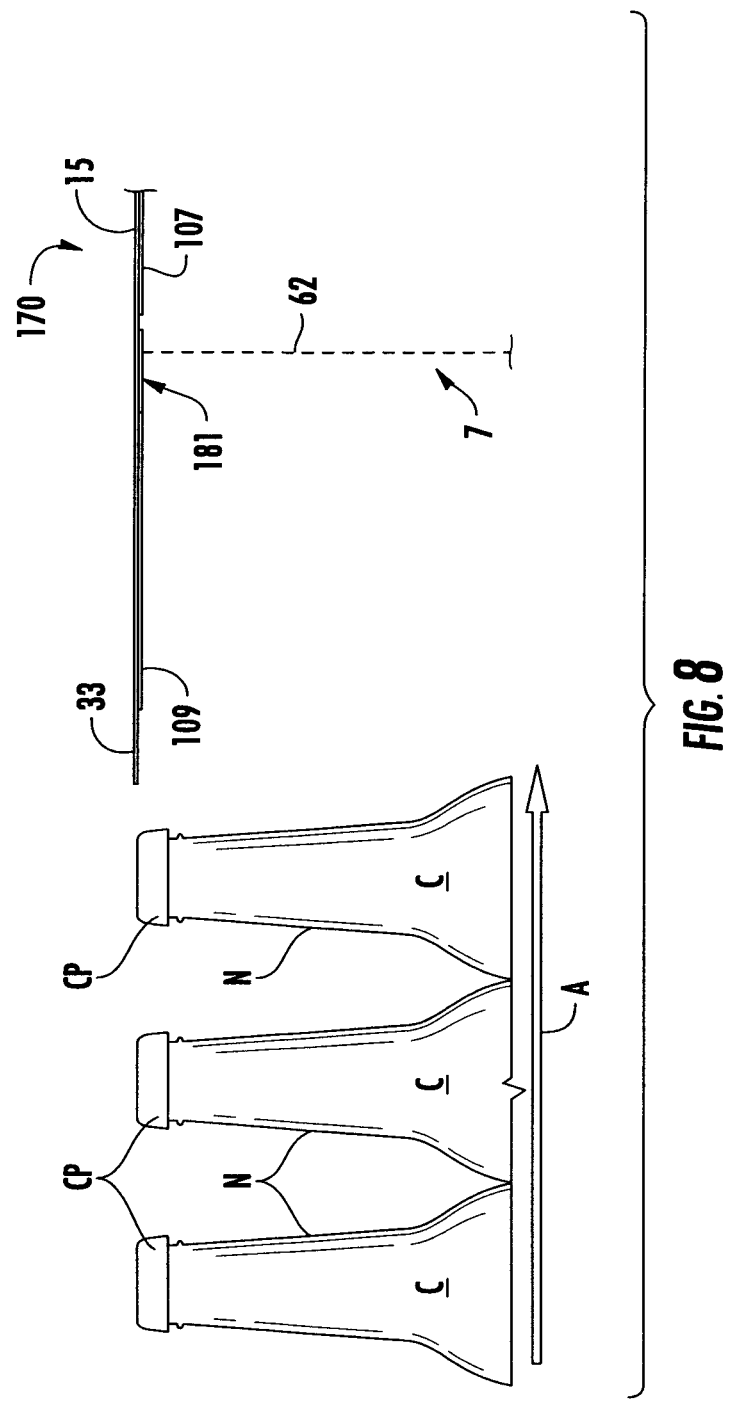
Figure 9:
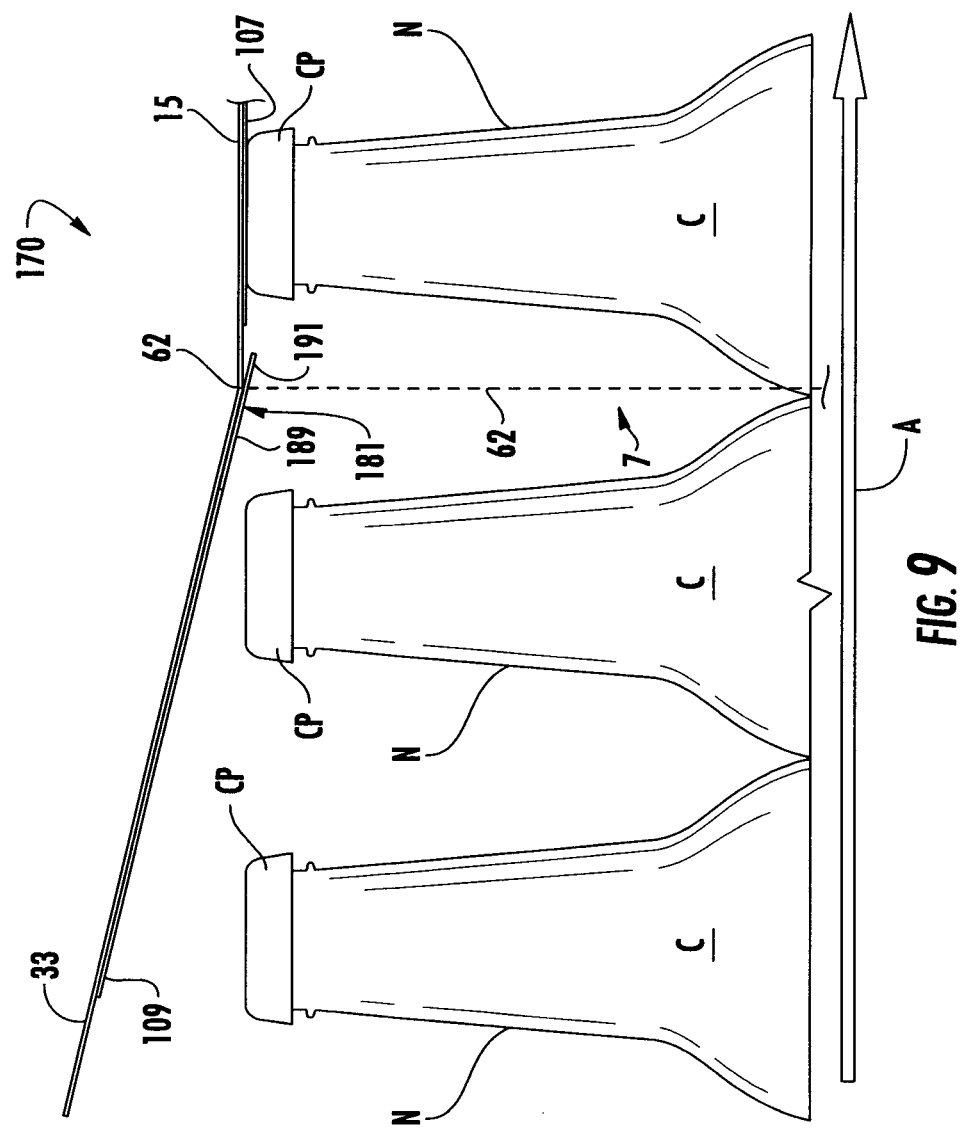

In accordance with the exemplary embodiment, the carton blank 3 with insert blank 103 can be further erected into the carton 5 by folding along fold lines 19, 23, 27, and 31 to form an open-ended sleeve 170 with an interior 172 (FIGS. 5 and 6). Containers C can be loaded into the interior 172 of the open-ended sleeve 170 as described further below (FIGS. 8-10). In one embodiment, the containers C could be loaded before or after closing either or both of the ends 7, 9 of the carton. The sleeve 170 could be otherwise formed without departing from the scope of this disclosure.

Figure 11:
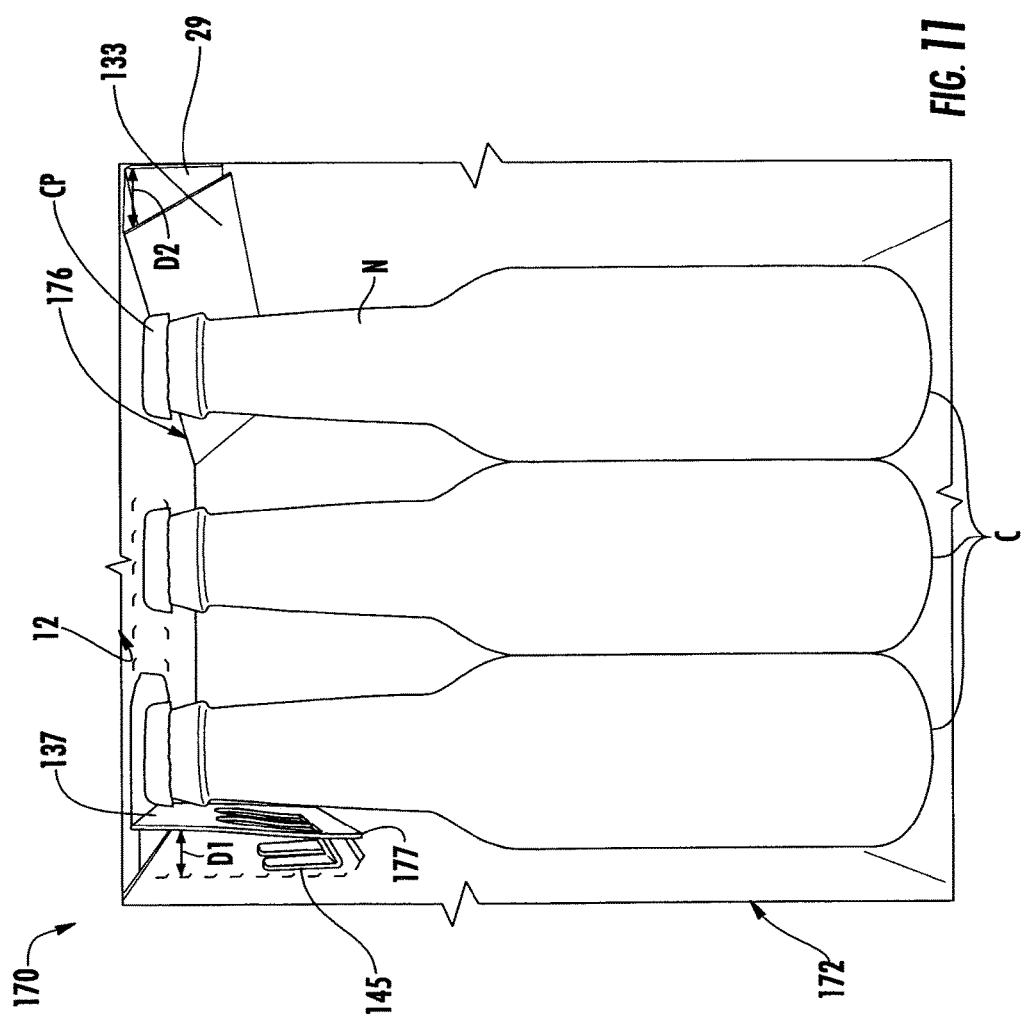
FIG. 11 is a perspective view of an interior of the carton formed from the insert blank and the carton blank according to the first exemplary embodiment of the disclosure.

In the illustrated embodiment, as the open-ended sleeve 170 is formed, the insert blank 103 is formed into the insert 12. Accordingly, as the outer side panels 17, 25 are folded with respect to the top panel 15 (e.g., so that the side panels 17, 25 are generally vertical and the top panel 15 is generally horizontal), the crown retention panel 137 can at least partially separate from the central panel 107 to extend at least partially into the interior 172 of the open-ended sleeve 170, generally parallel to the first side panel 17. As shown in FIGS. 6 and 11, the crown retention panel 137 can fold along the lateral fold line 139 and the lateral fold lines 147, 153 so that the crown retention panel 137 is at least partially spaced apart from the second side panel 17 by the distance D1 (FIGS. 6 and 11) into the interior 172 of the sleeve 170. In the illustrated embodiment, as the crown retention panel 137 separates from the central panel 107 along cut line 143, an opening 173 (FIG. 6) is formed in the central panel 107. An interior edge 174 of the central panel 107 extends adjacent to the opening 173, and the top panel 15 can be visible through the opening 173. The cut line 143 also forms an outer edge 175 of the crown retention panel 137. The outer edge 175 can have a lowermost portion 177 (e.g., lowermost edge) as shown in FIGS. 6 and 11. In one embodiment, the attachment flaps 145 separate from the crown retention flap 137 along the respective cut lines 155 and remain attached to the first side panel 17 (FIGS. 6 and 11) to help stabilize the lower portion of the crown retention panel 137.

As shown in FIGS. 6 and 11, the side flap 133 can fold along the lateral fold line 135, which is spaced apart from the second side panel 25 by the distance D2 (FIGS. 6 and 11). Accordingly, the side flap 133 can extend obliquely between the top panel 15 and the second side panel 25 in the interior 172 of the carton. As shown in FIG. 11, the crown retention panel 137 and the inner side flap 133 can contact the upper portions N and/or caps CP of the containers C that are adjacent the respective side panels 17, 25 to help restrain the narrower upper portions N of the containers. The crown retention panel 137 and the inner side flap 133 could be otherwise shaped, arranged, and/or configured without departing from the disclosure.

Figure 7:
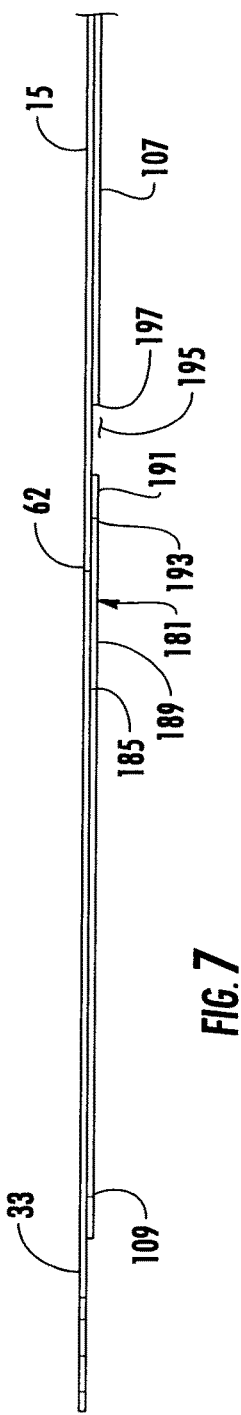
FIGS. 7-10 are schematic side views of the open-ended sleeve of FIG. 5 showing the formation of a crown retention feature according to the first exemplary embodiment of the disclosure.

The cross-sectional view of the top panel 15, the top end flap 33, the central panel 107, the inner end flap 109, the crown guard flap 181, and the crown guard relief 195 is schematically shown in FIG. 7. The containers C can be inserted into the sleeve 170 through the open end 7 as schematically shown in FIGS. 8 and 9 in one exemplary embodiment. Accordingly, as the containers C pass through the open end 7, the top end flap 33 and the inner end flap 109 can be folded upwardly along the respective fold lines 62, 113 (FIG. 8) to help avoid catching the tops of the containers C on the outer edges of the top end flap 33 and the inner end flap 109. With the top end flap 33 and the inner end flap 109 upwardly folded, the crown guard flap 181 can separate from the central panel 107 and the top panel 15 so that at least a portion of the second portion 191 and/or the first portion 189 extends below the top panel 15 and the central panel 107 as schematically shown in FIG. 8. While the crown guard flap 181 extends into the interior of the sleeve 170, it is directed away from the open end, generally in the direction of the loading of the containers C through the end 7 (e.g., along arrow A). Accordingly, as the containers C are inserted into the sleeve 170 in the direction of arrow A, the tops of the containers can push the crown guard flap 181 out of the way as they pass through the open end 7. In contrast, the tops of the containers could catch on the edge of an alternative flap that is connected to the central panel 107 and that extends towards the open end 7. The containers C can be loaded through one or both ends 7, 9, and either end 7, 9 could be closed before or after loading the containers C. The containers C could be loaded by alternative steps without departing from the disclosure.

Figure 12:
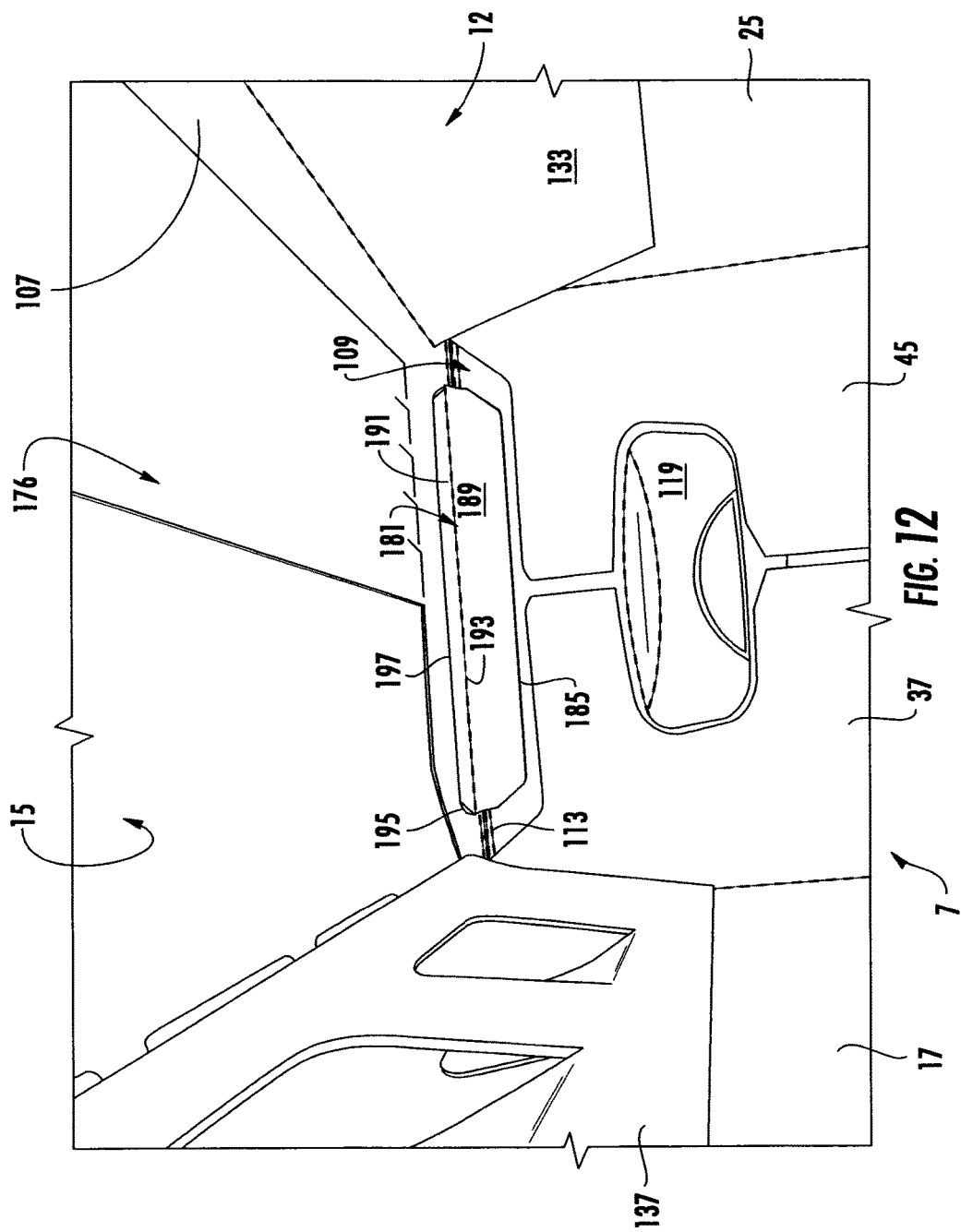
FIG. 12 is an interior perspective view of the carton formed from the insert blank and the carton blank according to the first exemplary embodiment of the disclosure.
Figure 13:
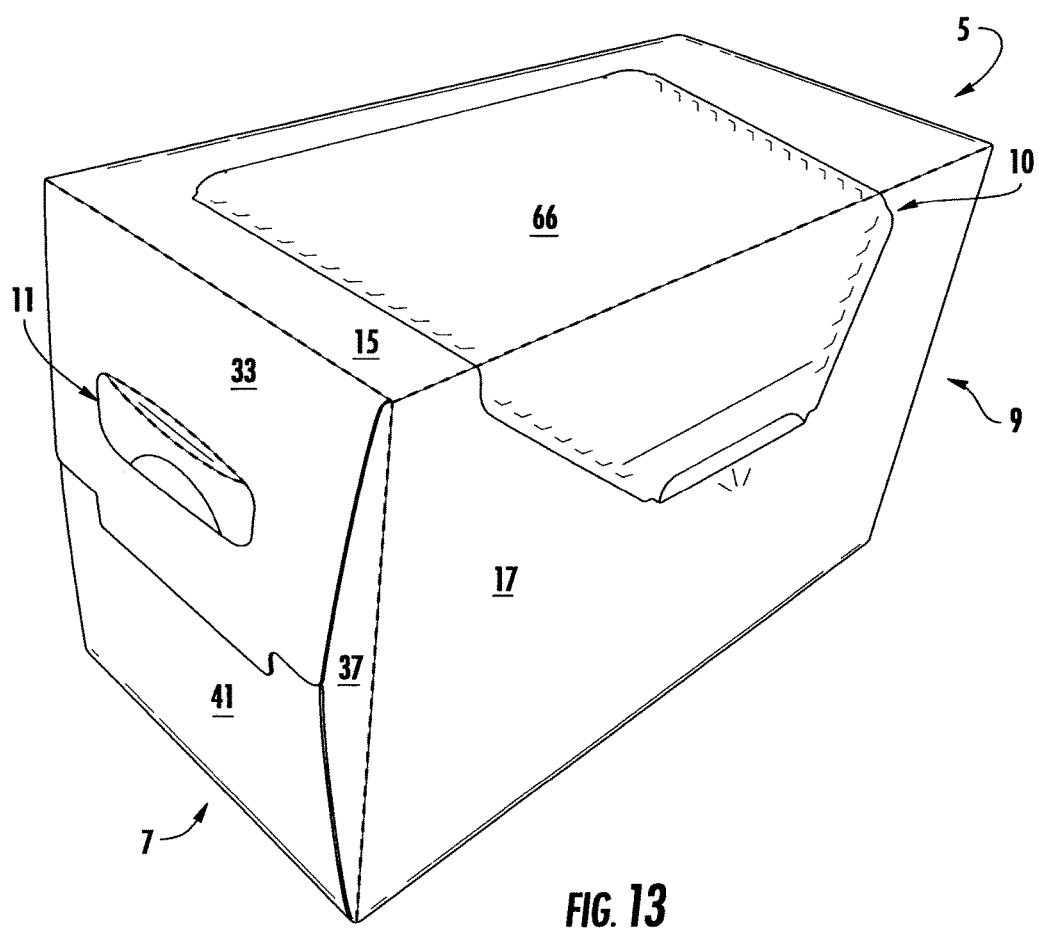
FIG. 13 is a perspective view of the erected carton according to the first exemplary embodiment of the disclosure.

In one embodiment, the ends 7, 9 of the carton 5 can be closed as shown in FIGS. 12 and 13. The side end flaps 37, 45 can be inwardly folded to at least partially close the first end 7. In the exemplary embodiment, the top end flap 33 and the inner end flap 109 can be downwardly folded and the bottom end flap 41 can be upwardly folded to overlap the side end flaps 37, 45 and to further at least partially close the first end 7. When the top end flap 33 and the inner end flap 109 overlap the side end flaps 37, 45, the inner and outer handle flaps 119, 49 are generally aligned with the cutouts 61 in the side end flaps to form the handle 11. Accordingly, a user can grasp the carton 5 at the handle 11 by folding the handle flaps 49, 119 into the interior 172 of the carton to form a handle opening (not shown). In the illustrated embodiment, the second end 9 can be closed in a similar or identical manner as the first end 7, and the handle 11 in the second end 9 can be formed in a similar manner as the handle 11 in the first end 7. The first end 7 and/or the second end 9 could be closed by other steps without departing from the disclosure. Further, the handles 11 could be formed by other steps without departing from the disclosure.

As shown in FIG. 11, the containers C can be restrained at the narrower upper portions N by the crown retention panel 137 and the side flap 133. As schematically shown in FIG. 10, the crown guard flap 181 can further restrain the upper portions N of the containers C adjacent the end 7 when the top end flap 33 and the inner end flap 109 are closed over the end 7. The side end flaps 37, 45 are omitted in the schematic view of FIG. 10 for clarity. In one embodiment, as the top end flap 33 and the inner end flap 109 are folded downwardly with respect to the top panel 15 and the central panel 107 (e.g., after folding the side end flaps 37, 45 over the end 7 as shown in FIG. 12), the first portion 189 of the crown guard flap 181 can separate from the top end flap 33 and the top panel 15, folding along the fold line 185 so that the first portion 189 extends obliquely between the top end flap 33 and the top panel 15. The second portion 191 of the crown guard flap 181 can fold along the fold line 193 so that the second portion 191 can be generally in face-to-face contact with the top panel 15 and slide along the top panel 15 until the edge of the second portion 191 engages the stop edge 197 of the central panel 107 (FIGS. 10 and 12). As shown in FIG. 10, the second portion 191 and the fold line 193 can be spaced apart from the top end flap 33 and the closed end 7 by a distance D3, and the crown guard flap 181 can engage the tops CP of the containers C adjacent the end 7 of the carton 5 (e.g., at or near the fold lines 193). Accordingly, the crown guard flap 181 can help retain the containers C in the carton 5. The second end 9 of the carton 5 with the crown guard flap 183 can be closed in similar manner as the first end 7, and the crown guard flap 183 can similarly restrain the upper portions N of the containers C adjacent the end 9. The ends 7, 9 of the carton 5 could be otherwise formed without departing from the scope of the disclosure. Additionally, the carton 5 and the insert 12 could be otherwise formed without departing from the scope of the disclosure.

The erected carton 5 according to the exemplary embodiment is shown in FIG. 13. In the exemplary embodiment, the crown retention panel 137, the inner side flap 133, the crown guard flaps, and/or other crown guard features can help provide an upper portion or crown area 176 (FIG. 12) of the carton 5 that is smaller than the lower portion of the carton to help restrain the narrower upper portions N of the containers C. In one embodiment, the article protection flaps 13 in the bottom panel 21 also help restrain movement of the containers C.

In the illustrated embodiment, a user can grasp and carry the carton 5 at the handles 11 by folding the outer handle flaps 49 and the inner handle flaps 119 into the interior 172 of the carton to form handle openings (not shown) in the ends 7, 9 of the carton. The dispenser 10 can be can be opened by tearing the dispenser panel 66 away along the tear lines 67 to form a dispenser opening (not shown) in the top panel 15 and the side panel 17 of the carton 5. The tearing of the dispenser panel can be initiated, for example, at the access panel 69. In one embodiment, as shown by way of example in FIG. 9, the dispenser portion 159 of the central panel 107 of the insert 12 defined between the tear lines 161 can be glued to the portion of the dispenser panel 66 in the top panel 15. Accordingly, when the dispenser panel 66 is torn away, the central panel 107 can tear along the tear lines 161 and can fold along the fold line 163. Additionally, the crown retention panel 137, which can be attached to the dispenser panel 66 via the attachment flaps 145, can be pulled out of the interior of the carton as the dispenser panel 66 is pivoted upwardly along the fold line 68 to help provide access to the containers C. The handles 11 and/or the dispenser panel 10 could be otherwise actuated without departing from the disclosure.

Figure 14:
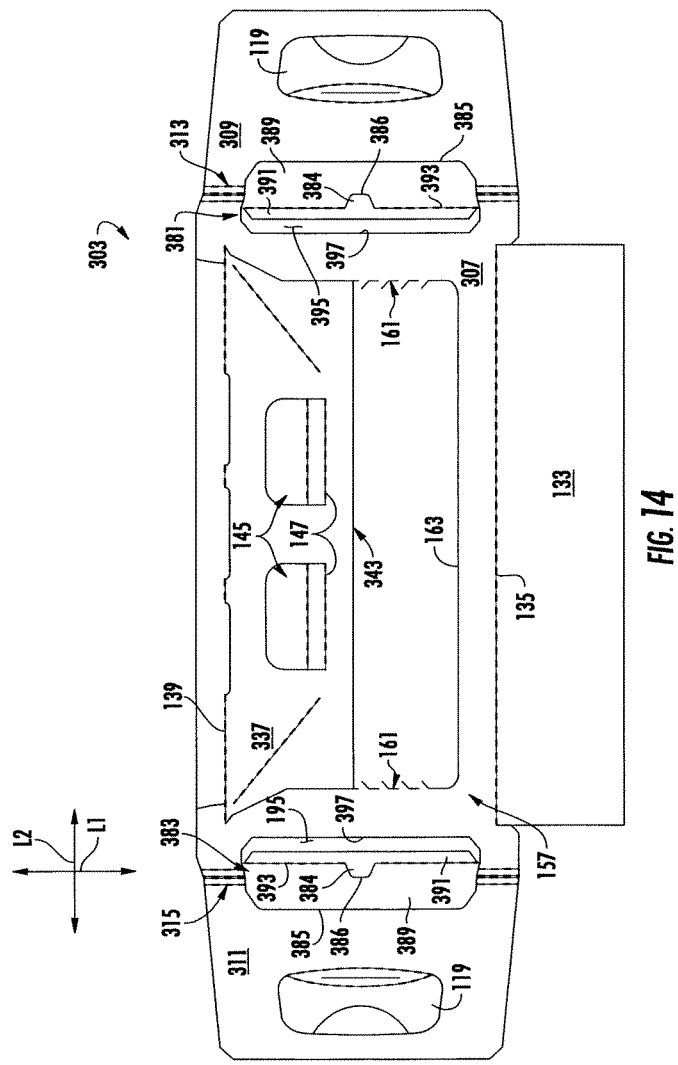
FIG. 14 is a plan view of an insert blank for forming an insert according to a second exemplary embodiment of the disclosure.
Figure 18:
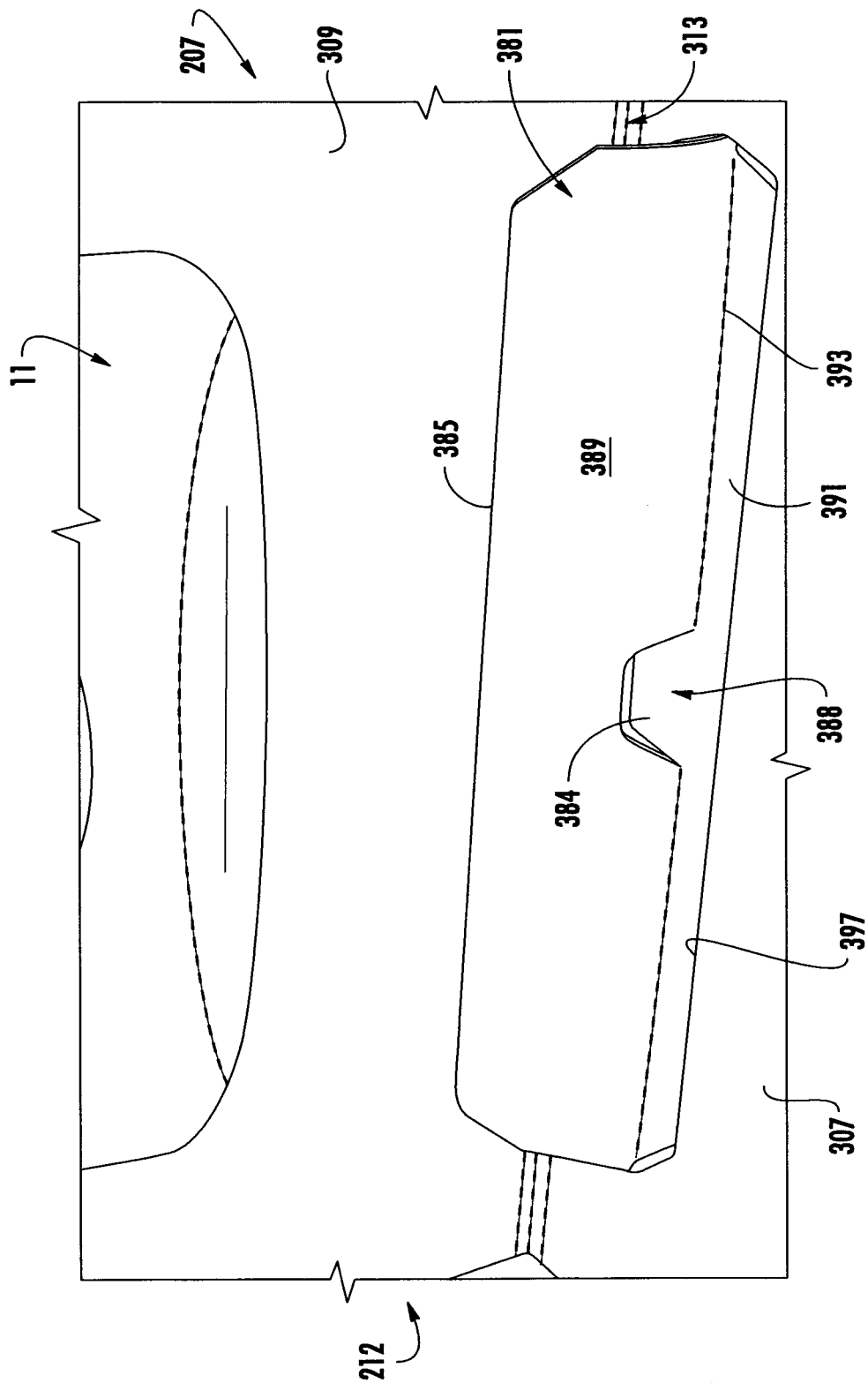
FIG. 18 is an interior perspective view showing the configuration of the crown guard feature of FIG. 17.

FIG. 14 is a plan view of an insert blank 303 for forming an insert 212 (FIGS. 17 and 18) according to a second embodiment of the disclosure. The insert 212 of the second embodiment is generally similar to the insert of the first embodiment, except for variations noted and variations that will be apparent to one of ordinary skill in the art. Accordingly, similar or identical features of the embodiments have been given like or similar reference numbers. As shown in FIG. 14, the crown retention panel 337 can be defined by a tear or cut line 343 that has a different shape than the cut line 143 of the first embodiment. Further, the crown guard flaps 381, 383 include respective tabs 384 extending from the respective second portions 391 into the respective first portions 389. The tabs 384 can be at least partially defined by generally U-shaped tear lines or cuts 386 that interrupt the respective fold lines 393. When the insert 212 is formed, the tabs 384 can form respective crown lock apertures 388 (FIG. 18). The crown guard flaps 381, 383, the tabs 384, and/or the cuts 386 could be otherwise shaped, arranged, and/or configured without departing from the disclosure. Additionally, the insert blank 303 could be otherwise shaped, arranged, and/or configured without departing from the disclosure.

Figure 15:
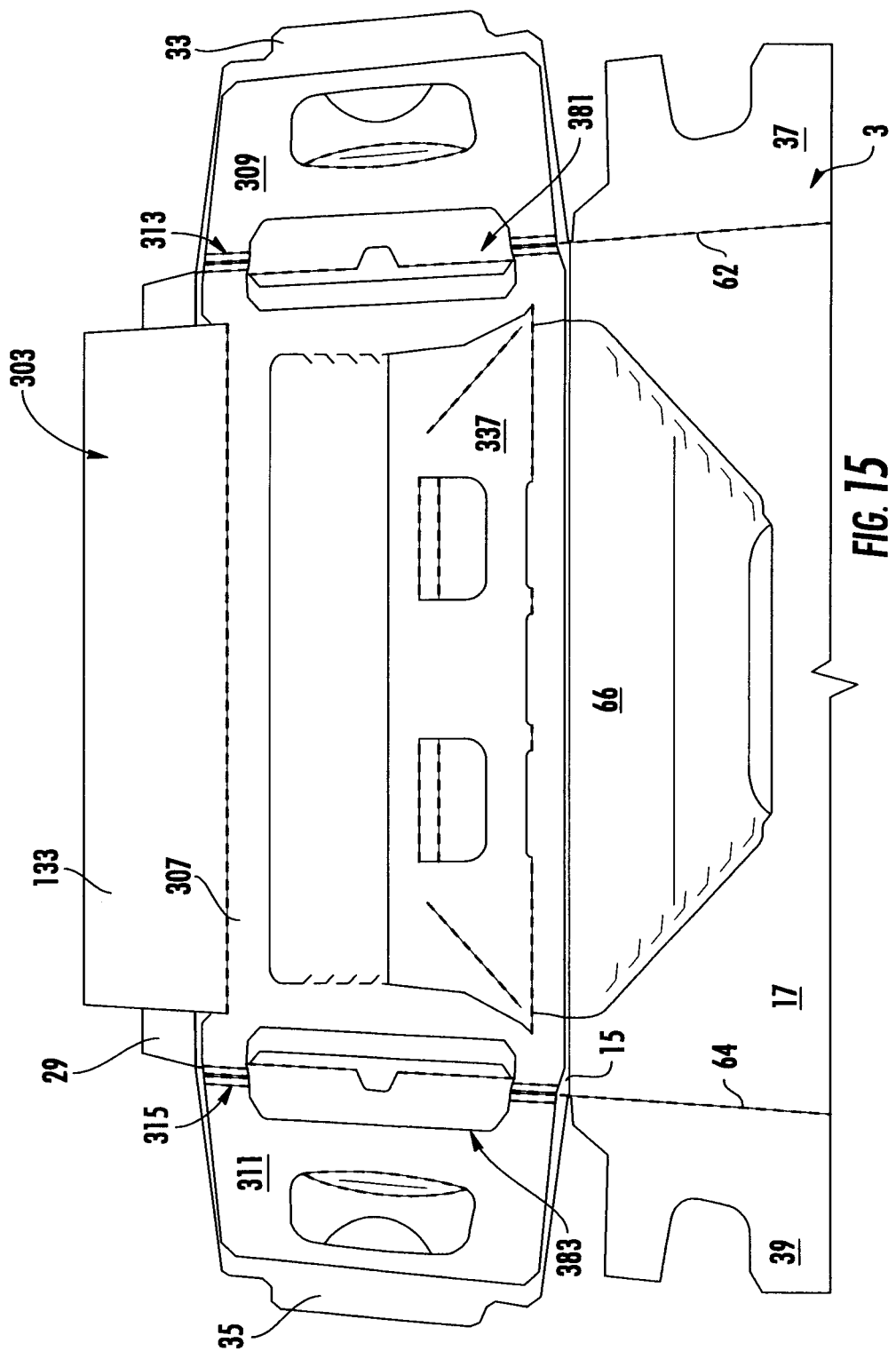
FIG. 15 is a plan view of the insert blank of FIG. 14 in combination with the carton blank of FIG. 1 according to the second exemplary embodiment of the disclosure.

As shown in FIGS. 15 and 16, in one embodiment, the insert blank 303 can be overlapped with and/or glued to the carton blank 3 of the first embodiment, or any other suitable carton blank. The insert blank 303 can be aligned with the top panel 15 and the top end flaps 33, 35 of the carton blank 3 similarly to the insert blank 103 of the first embodiment and formed into a sleeve (not shown) with the insert 212 therein. FIGS. 16 and 17 schematically show the closing of one of the ends (e.g., a first end 207) of the carton (not shown) and the interaction between the crown guard flap 381 and the tops of the containers C in one embodiment. Accordingly, as the top end flap 33 and the inner end flap 309 are folded downwardly with respect to the top panel 15 and the central panel 307, the first portion 389 of the crown guard flap 381 can separate from the top end flap 33 and the top panel 15, folding along the fold line 385 so that the first portion extends obliquely between the top end flap 33 and the top panel 15. The second portion 391 of the crown guard flap 381 can fold along the fold line 393 so that the tab 384 separates from the first portion 389 at the cut 386 and the second portion 391 and the tab 384 remain generally in face-to-face contact with the top panel 15 and slide along the top panel 15 until the edge of the second portion 391 engages the stop edge 397 of the central panel 307 (FIG. 17).

As shown in FIG. 17, wherein the side end flaps 37, 45 are omitted for clarity, the crown guard flap 381 can engage the top CP of one of the containers C adjacent the end 207 of the carton in the crown lock aperture 388 (FIG. 18). Accordingly, the top CP of one of the containers C can be at least partially received in the crown lock aperture 388, and, in one embodiment, an edge of the first portion 389 of the crown guard flap 381 adjacent the crown lock aperture 388 can engage under the rim of the top CP. The other containers C adjacent the end 209 also can be engaged by the crown guard flap 381 (e.g., at or near the fold lines 393). Accordingly, the crown guard flap 381 can help retain the containers C in the carton. As shown in FIG. 17, the fold line 393 can be spaced apart from the top end flap 33 by the distance D3 similarly to that shown in the first embodiment. Additionally, in one embodiment, the tab 384 can be spaced apart from the top end flap 33 by a distance D4 that is generally shorter than distance D3, as shown in FIG. 17. The second end of the carton (not shown) can be closed in a similar manner as the first end 207. The ends of the carton could be otherwise formed without departing from the scope of the disclosure. Additionally, the carton and the insert 212 could be otherwise formed without departing from the scope of the disclosure. For example, one or both of the crown guard flaps 381, 383 could include a tab 384 and a crown lock aperture 388 for each of the containers C adjacent the end 207 (e.g., three tabs 384 and three crown lock apertures 388 for a 3×6 carton).

Figure 19:
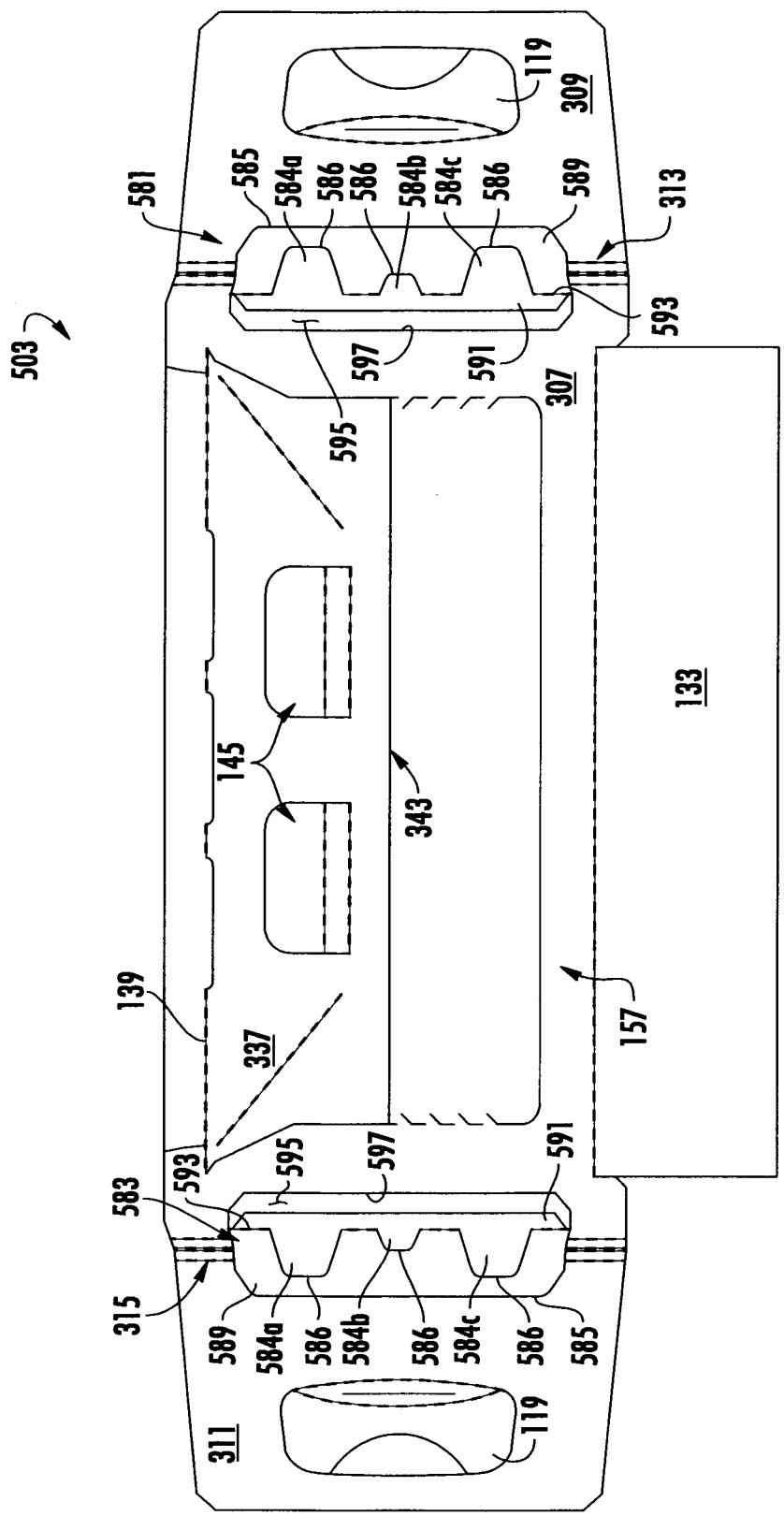
FIG. 19 is a plan view of an insert blank for forming an insert according to a third exemplary embodiment of the disclosure.

FIG. 19 is a plan view of an insert blank 503 for forming an insert 412 (FIGS. 22 and 23) according to a third embodiment of the disclosure. The insert of the third embodiment is generally similar to the insert of the second embodiment, except for variations noted and variations that will be apparent to one of ordinary skill in the art. Accordingly, similar or identical features of the embodiments have been given like or similar reference numbers. As shown in FIG. 19, each of the crown guard flaps 581, 583 includes three tabs 584a, 584b, 584c extending from the respective second portion 591 into the respective first portion 589. Each of the tabs 584a, 584b, 584c can be at least partially defined by a generally U-shaped tear line or cut 586 that interrupts the respective fold lines 593. When the insert 412 is formed, the tabs 584a, 584b, 584c can form respective apertures 588a, 588b, 588c (FIG. 23). In one embodiment, the aperture 588b can be a crown lock aperture similar to the crown lock aperture 388 of the second embodiment. The crown guard flaps 581, 583, the tabs 584a, 584b, 584c, and/or the cuts 586 could be otherwise shaped, arranged, and/or configured without departing from the disclosure. Additionally, the insert blank 503 could be otherwise shaped, arranged, and/or configured without departing from the disclosure.

As shown in FIGS. 20 and 21, in one embodiment, the insert blank 503 can be overlapped with and/or glued to the carton blank 3 of the first embodiment, or any other suitable carton blank. The insert blank 503 can be aligned with the top panel 15 and the top end flaps 33, 35 of the carton blank 3 similarly to the insert blank 103 of the first embodiment and formed into a sleeve (not shown) with the insert 412 therein. FIGS. 21 and 22 schematically show the closing of one of the ends (e.g., a first end 407) of the carton (not shown) and the interaction between the crown guard flap 581 and the tops of the containers C in one embodiment. The closing of the end 407 can be similar to that shown and described in the second embodiment above except that the tabs 584a, 584b, 584c in the crown guard flap 581 separate from the first portion 589 at the cuts 586 to form the respective apertures 588a, 588b, 588c. As noted above the aperture 588b can be a crown lock aperture receiving the top of a containers C adjacent the end 407 (e.g., the middle container at the end 407). When the tabs 584a, 584c separate from the first portion 589, they can extend the distance D3 from the fold line 593 to abut the downwardly-extending top end flap 33 (e.g., the tab 584a is schematically shown extending from the fold line 593 to the top end flap 33 in FIG. 22). Accordingly, the tabs 584a, 584c form stops that can help force the first portion 591 against the stop edge 597 of the center panel 307. In an alternative embodiment, the apertures 588a, 588c can be sized and positioned to form additional crown lock apertures for receiving additional containers C at the end 407. The second end of the carton (not shown) can be closed in a similar manner as the first end 407. The ends of the carton could be otherwise formed without departing from the scope of the disclosure. Additionally, the carton and the insert 412 could be otherwise formed without departing from the scope of the disclosure.

Figure 24:
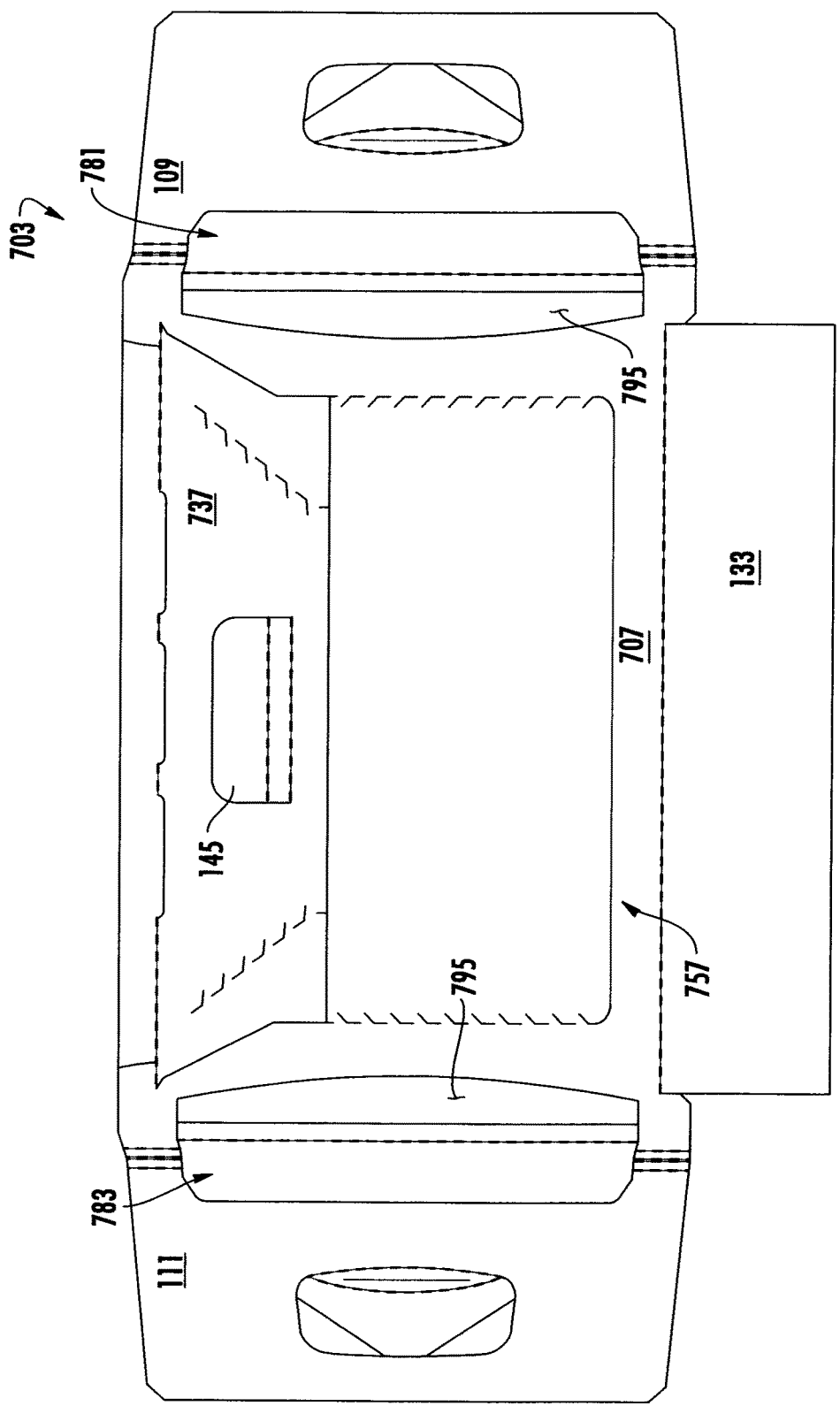
FIG. 24 is a plan view of an insert blank for forming an insert according to a fourth exemplary embodiment of the disclosure.

FIG. 24 is a plan view of an insert blank 703 for forming an insert (not shown) according to a fourth embodiment of the disclosure. The insert of the fourth embodiment is generally similar to the insert of the first embodiment, except for variations noted and variations that will be apparent to one of ordinary skill in the art. Accordingly, similar or identical features of the embodiments have been given like or similar reference numbers. As shown in FIG. 24, the crown retention panel 737 includes one attachment flap 145, and the dispenser pattern 757 includes two tear lines extending in the crown retention panel 737. The crown guard flaps 781, 783 generally are similar to the crown guard flaps 181, 183 of the first embodiment, but have a generally different shape. The insert blank 703 could be otherwise shaped, arranged, and/or configured without departing from the disclosure.

Figure 25:
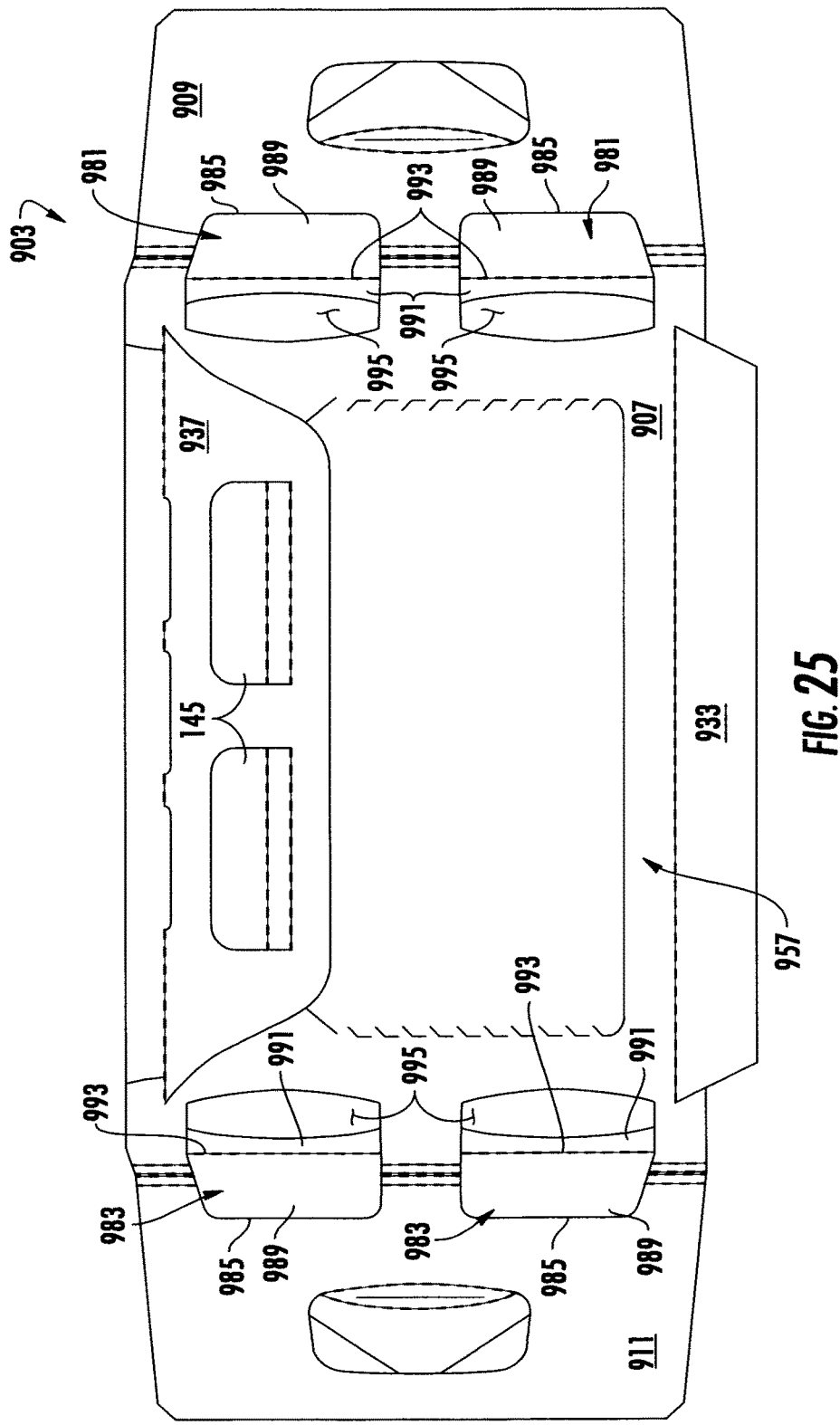
FIG. 25 is a plan view of an insert for forming an insert according to a fifth exemplary embodiment of the disclosure.

FIG. 25 is a plan view of an insert blank 903 for forming an insert (not shown) according to fifth embodiment of the disclosure. The insert of the fifth embodiment is generally similar to the insert of the fourth embodiment, except for variations noted and variations that will be apparent to one of ordinary skill in the art. Accordingly, similar or identical features of the embodiments have been given like or similar reference numbers. As shown in FIG. 25, the insert blank 903 includes two crown guard flaps 981 foldably connected to the first inner end flap 909 along respective fold lines 985 and two crown guard flaps 983 foldably connected to the second inner end flap 911 along respective fold lines 985. Each of the crown guard flaps 981, 983 includes a first portion 989 and a second portion 991 foldably connected to the respective first portion 989 along a fold line 993. Each of the crown guard flaps 981, 983 extends adjacent a respective crown guard opening or relief 995. When the insert (not shown) is formed in the carton (not shown), each of the crown guard flaps 981, 983 can engage one or more containers C similarly to the crown guard flaps of the above embodiments. As shown in FIG. 25, the crown retention panel 937, the inner side flap 933, and the inner dispenser pattern 957 can have different shapes than the respective features in the other embodiments. The insert blank 903 could be otherwise shaped, arranged, and/or configured without departing from the disclosure. For example, any suitable number of crown guard flaps can be foldably connected to each of the inner end flaps 909, 911.

Any of the features of the various embodiments of the disclosure can be combined with, replaced by, or otherwise configured with other features of other embodiments of the disclosure (and/or the disclosures that have been incorporated by reference) without departing from the scope of this disclosure. Further, it is noted that the inserts, insert blanks, and/or crown retention features of the various embodiments can be incorporated into a carton having any carton style or panel configuration. The carton styles and panel configurations described above are included by way of example.

The blanks according to the present disclosure can be, for example, formed from coated paperboard and similar materials. For example, the interior and/or exterior sides of the blanks can be coated with a clay coating. The clay coating may then be printed over with product, advertising, price coding, and other information or images. The blanks may then be coated with a varnish to protect any information printed on the blank. The blanks may also be coated with, for example, a moisture barrier layer, on either or both sides of the blank. In accordance with the above-described embodiments, the blanks may be constructed of paperboard of a caliper such that it is heavier and more rigid than ordinary paper. The blanks can also be constructed of other materials, such as cardboard, hard paper, or any other material having properties suitable for enabling the carton to function at least generally as described herein. The blanks can also be laminated or coated with one or more sheet-like materials at selected panels or panel sections.

In accordance with the above-described embodiments of the present disclosure, a fold line can be any substantially linear, although not necessarily straight, form of weakening that facilitates folding therealong. More specifically, but not for the purpose of narrowing the scope of the present disclosure, fold lines include: a score line, such as lines formed with a blunt scoring knife, or the like, which creates a crushed portion in the material along the desired line of weakness; a cut that extends partially into a material along the desired line of weakness, and/or a series of cuts that extend partially into and/or completely through the material along the desired line of weakness; and various combinations of these features.

As an example, a tear line can include: a slit that extends partially into the material along the desired line of weakness, and/or a series of spaced apart slits that extend partially into and/or completely through the material along the desired line of weakness, or various combinations of these features. As a more specific example, one type tear line is in the form of a series of spaced apart slits that extend completely through the material, with adjacent slits being spaced apart slightly so that a nick (e.g., a small somewhat bridging-like piece of the material) is defined between the adjacent slits for typically temporarily connecting the material across the tear line. The nicks are broken during tearing along the tear line. The nicks typically are a relatively small percentage of the tear line, and alternatively the nicks can be omitted from or torn in a tear line such that the tear line is a continuous cut line. That is, it is within the scope of the present disclosure for each of the tear lines to be replaced with a continuous slit, or the like. For example, a cut line can be a continuous slit or could be wider than a slit without departing from the present disclosure.

The above embodiments may be described as having one or more panels adhered together by glue during erection of the carton embodiments. The term "glue" is intended to encompass all manner of adhesives commonly used to secure carton panels in place.

The foregoing description of the disclosure illustrates and describes various embodiments. As various changes could be made in the above construction without departing from the scope of the disclosure, it is intended that all matter contained in the above description or shown in the accompanying drawings shall be interpreted as illustrative and not in a limiting sense. Furthermore, the scope of the present disclosure covers various modifications, combinations, alterations, etc., of the above-described embodiments that are within the scope of the claims. Additionally, the disclosure shows and describes only selected embodiments of the disclosure, but the disclosure is capable of use in various other combinations, modifications, and environments and is capable of changes or modifications within the scope of the inventive concept as expressed herein, commensurate with the above teachings, and/or within the skill or knowledge of the relevant art. Furthermore, certain features and characteristics of each embodiment may be selectively interchanged and applied to other illustrated and non-illustrated embodiments of the disclosure.

What is claimed is:

1. A carton for holding a plurality of containers, the carton comprising:
   a plurality of panels that extends at least partially around an interior of the carton, the plurality of panels comprising a top panel; and
   an insert comprising a central panel, an inner end flap foldably connected to the central panel, and at least one crown guard flap foldably connected to the inner end flap adjacent a crown guard opening in the insert, the central panel comprising a stop edge adjacent the crown guard opening, and the crown guard flap comprising a first portion foldably connected to the inner end flap and a second portion foldably connected to the first portion;
   wherein the top panel of the plurality of panels at least partially overlaps the central panel of the insert, the second portion of the crown guard flap is at least partially in contact with the top panel of the plurality of panels, and the second portion of the crown guard flap is disposed adjacent the stop edge of the central panel.

2. The carton of claim 1, wherein the crown guard flap is configured to be in contact with at least one container of the plurality of containers when the plurality of containers are held in the interior of the carton, and at least a portion of the first portion of the crown guard flap extends obliquely with respect to the inner end flap and the central panel.

3. The carton of claim 2, wherein at least a portion of the second portion of the crown guard flap is configured to be disposed between a top portion of the at least one container and the top panel when the plurality of containers are held in the interior of the carton.

4. The carton of claim 1, wherein the second portion of the crown guard flap is at least partially in face-to-face contact with the top panel.

5. The carton of claim 1, wherein the inner end flap is foldably connected to the central panel along a fold line, the fold line being interrupted by the crown guard opening.

6. The carton of claim 5, wherein the fold line is a first fold line, and the first portion of the crown guard flap is foldably connected to the inner end flap along a second fold line that is spaced apart from the first fold line and the central panel.

7. The carton of claim 6, wherein the second portion of the crown guard flap is foldably connected to the first portion along a third fold line that is spaced apart from the inner end flap and the first fold line.

8. A carton for holding a plurality of containers, the carton comprising:
   a plurality of panels that extends at least partially around an interior of the carton, the plurality of panels comprising a top panel; and
   an insert comprising a central panel, an inner end flap foldably connected to the central panel, and at least one crown guard flap foldably connected to the inner end flap adjacent a crown guard opening in the insert, the central panel comprising a stop edge adjacent the crown guard opening, and the crown guard flap comprising a first portion foldably connected to the inner end flap and a second portion foldably connected to the first portion;
   wherein the top panel at least partially overlaps the central panel, and the second portion of the crown guard flap is disposed adjacent the stop edge of the central panel;
   wherein the second portion of the crown guard flap is foldably connected to the first portion of the crown guard flap along a fold line, and the crown guard flap comprises a tab extending from the second portion adjacent an aperture in the first portion, the aperture and the tab interrupting the fold line.

9. The carton of claim 8, wherein the aperture is a crown lock aperture for receiving and at least partially engaging at least a portion of at least one container of the plurality of containers.

10. The carton of claim 9, wherein at least a portion of the second portion and the tab of the crown guard flap is for being disposed between a top portion of the at least one container and the top panel.

11. The carton of claim 8, wherein the tab extends from the second portion of the crown guard flap toward the inner end flap.

12. The carton of claim 11, further comprising at least a top end flap foldably connected to the top panel and at least partially overlapping the inner end flap, wherein the tab abuts the top end flap to urge at least a portion of the second portion of the crown guard flap against the stop edge of the central panel.

13. The carton of claim 8, wherein the tab is a first tab, the aperture is a first aperture, and the crown guard flap comprises at least a second tab extending from the second portion adjacent a second aperture.

14. The carton of claim 13, further comprising at least a top end flap foldably connected to the top panel and at least partially overlapping the inner end flap, wherein the first tab is spaced apart from the top end flap, and the second tab abuts the top end flap to urge at least a portion of the second portion of the crown guard flap against the stop edge of the central panel.

15. The carton of claim 1, wherein the crown guard flap is a first crown guard flap, the crown guard opening is a first crown guard opening, and the insert comprises a second crown guard flap foldably connected to the inner end flap adjacent a second crown guard opening.

16. The carton of claim 15, wherein the first portion and the second portion of the first crown guard flap comprise a first proximal portion and a first distal portion, respectively, and the second crown guard flap comprises a second proximal portion foldably connected to the inner end flap and a second distal portion foldably connected to the second proximal portion.

17. The carton of claim 1, further comprising a plurality of end flaps respectively foldably connected to respective panels of the plurality of panels, the plurality of end flaps being at least partially overlapped with respect to one another to thereby at least partially form a closed end of the carton, the plurality of end flaps comprising a top end flap foldably connected to the top panel and at least partially overlapping the inner end flap.

18. A carton for holding a plurality of containers, the carton comprising:
a plurality of panels that extends at least partially around an interior of the carton, the plurality of panels comprising a top panel;
an insert comprising a central panel, an inner end flap foldably connected to the central panel, and at least one crown guard flap foldably connected to the inner end flap adjacent a crown guard opening in the insert, the central panel comprising a stop edge adjacent the crown guard opening, and the crown guard flap comprising a first portion foldably connected to the inner end flap and a second portion foldably connected to the first portion;
a plurality of end flaps respectively foldably connected to respective panels of the plurality of panels, the plurality of end flaps being at least partially overlapped with respect to one another to thereby at least partially form a closed end of the carton, the plurality of end flaps comprising a top end flap foldably connected to the top panel and at least partially overlapping the inner end flap; and
a handle formed in the closed end, the handle extending in at least the top end flap and the inner end flap;
wherein the top panel at least partially overlaps the central panel, and the second portion of the crown guard flap is disposed adjacent the stop edge of the central panel.

19. The carton of claim 18, wherein the handle comprises at least one handle flap foldably connected to at least one of the top end flap and the inner end flap.

20. A carton for holding a plurality of containers, the carton comprising:
a plurality of panels that extends at least partially around an interior of the carton, the plurality of panels comprising a top panel; and
an insert comprising a central panel, an inner end flap foldably connected to the central panel, and at least one crown guard flap foldably connected to the inner end flap adjacent a crown guard opening in the insert, the central panel comprising a stop edge adjacent the crown guard opening, and the crown guard flap comprising a first portion foldably connected to the inner end flap and a second portion foldably connected to the first portion;
wherein the top panel at least partially overlaps the central panel, and the second portion of the crown guard flap is disposed adjacent the stop edge of the central panel;
wherein the insert further comprises a crown retention panel foldably connected to the central panel and an attachment flap foldably connected to the crown retention panel.

21. The carton of claim 20, wherein the plurality of panels further comprises a side panel, at least a portion of the crown retention panel is spaced apart from the side panel in the interior of the carton, and at least a portion of the attachment flap is at least partially in face-to-face contact with the side panel.

22. The carton of claim 21, wherein crown retention panel is positioned for contact with at least one container of the plurality of containers.

23. The carton of claim 21, wherein the side panel is a first side panel, the carton further comprises a second side panel, and the insert further comprises a side flap foldably connected to the central panel along a lateral fold line, the side flap extending at least generally downwardly from the central panel and towards the second side panel in the interior of the carton.

* * * * *